United States Patent [19]

Tsukamoto et al.

[11] Patent Number: 4,629,736

[45] Date of Patent: Dec. 16, 1986

[54] FATTY ACID DERIVATIVES AND PROCESS OF PRODUCING THEM

[75] Inventors: Shin-ichi Tsukamoto; Yoshinobu Nagano, both of Tokyo; Kimio Katsuda, Saitama, all of Japan

[73] Assignee: Yamanouchi Pharmaceutical Co., Ltd., Tokyo, Japan

[21] Appl. No.: 656,165

[22] Filed: Sep. 28, 1984

[30] Foreign Application Priority Data

Sep. 30, 1983 [JP] Japan .................................. 58-182000
Jul. 24, 1984 [JP] Japan .................................. 59-153430

[51] Int. Cl.$^4$ ..................... C07C 103/52; A61K 37/02
[52] U.S. Cl. ..................................... 514/563; 260/401;
260/404; 260/404.5; 514/19; 514/546; 514/552;
514/558; 514/559; 514/560; 514/562; 514/578;
560/159; 560/167; 560/186; 560/187; 560/250;
560/253; 562/430; 562/440; 562/445; 562/448;
562/450; 562/556; 562/560; 562/561; 562/564;
562/567; 562/574; 562/575
[58] Field of Search ..................... 260/112.5 R, 404;
560/187, 253; 562/450, 575, 567, 564; 514/19,
552, 563, 551, 546

[56] References Cited

FOREIGN PATENT DOCUMENTS 54435 6/1982 European Pat. Off. .
85255 8/1983 European Pat. Off. .

OTHER PUBLICATIONS

Sen. J. Indian Chem. Soc., 41, pp. 137–141 (1964).

Primary Examiner—Michael L. Shippen
Attorney, Agent, or Firm—Burgess, Ryan & Wayne

[57] ABSTRACT

Fatty acid derivatives represented by the general formula

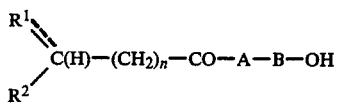

and salts thereof.

The compounds of this invention have excellent fibrinolytic action and a highly improved solubility.

10 Claims, No Drawings

FATTY ACID DERIVATIVES AND PROCESS OF PRODUCING THEM

FIELD OF THE INVENTION

This invention relates to fatty acid derivatives and salts thereof showing excellent fibrinolytic action and a highly improved water solubility. The invention further relates to processes of producing these fatty acid derivatives and salts thereof.

BACKGROUND OF THE INVENTION

As a prophylaxis or treatment method of thrombosis by dissolving the fibrin clot of arteriovenous thrombosis, a method of administering plasmin, a method of administering a plasminogen activator, a method of releasing a plasminogen activator by the administration of a medicament, a method of restraining a palsmin inhibitor, and the like, have been proposed and variously investigated but since these methods each of has some difficulties, only Urokinase is on the market as a fibrinolytic agent.

However, Urokinase has problems that the medicament cannot be orally administered, the medicament must be administered at a very high unit dosage, which results in increasing the cost of the medicament, and hence the development of compounds other than Urokinase, which can be orally administered and can be administered at a low cost, has been desired.

Hitherto, low molecular fibrinolytic agents which can be orally administered have been investigated but such fibrinolytic agents have not yet been practically used.

Recently, as one of the compounds possessing a fibrinolytic action, acylpeptides shown by the following general formulae (A) and (B) were proposed (European Patent Publication (Unexamined) Nos. 54,435 and 85,255);

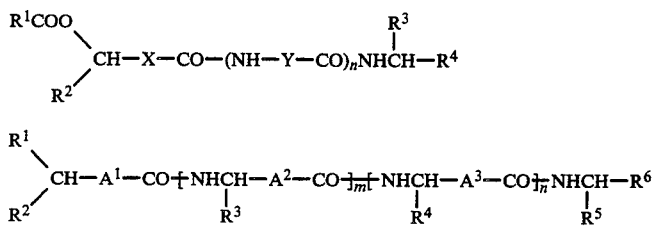

However, for the clinical use as a fibrinolytic agent, the foregoing compounds are still insufficient in fibrinolytic activity. Almost all the foregoing known compounds show a low solubility in water, which makes it difficult to attain the sufficient pharamcological activity of these compounds and to form the preparations of these compounds.

SUMMARY OF THE INVENTION

The object of this invention is, therefore, to provide novel compounds having excellent fibrinolytic activity and high solubility in water as compared to the foregoing known compounds.

As the result of synthesizing various novel fibrinolytic compounds and investigating the fibrinolytic activity of these compounds, it has been discovered that the compounds shown by following general formula (I) and the pharmaceutically acceptable salts of them are very excellent in fibrinolytic activity and show a high solubility in water, and based on the discovery, the invention has been accomplished.

That is, according to this invention, there is provided a fatty acid derivative represented by following general formula (I) or a salt thereof;

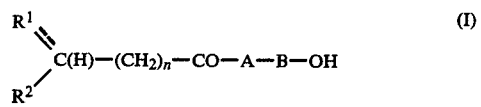

in which

R$^1$ represents an alkanoylamino group the carbon chain of which may be interrupted by at least one oxygen atom, an alkanoyloxy group the carbon chain of which is interrupted by at least one oxygen atom, an alkoxyimino group, or a group shown by R$^3$—(NH—Y—CO)$_m$—Z— (wherein R$^3$ represents an alkanoyl group or a lower alkylsulfonyl group; Y represents an alkylene group; m is 1 or 2; and Z represents an oxygen atom or an imino group);

R$^2$ represents an alkyl group, an alkylaminocarbonyl group the carbon chain of which may be interrupted by at least one oxygen atom, or an alkoxyaminocarbonyl group the carbon chain of which is interrupted by at least one oxygen atom = represents a single bond or a double bond;

(H) means that when = is a double bond, a hydrogen atom does not exist and when = is a single bond, a hydrogen atom exists;

n represents an integer of 1 to 3; and

A and B, which may be the same or different, each represents a single bond or an amino acid residue.

DESCRIPTION OF THE PREFERRED EMBODIMENT

In the definitions of the groups used for the indications of the general formulae in this specification, the term "lower" means a straight or branched carbon chain having 1 to 5 carbon atoms, unless otherwise indicated.

Accordingly, a lower alkyl group or lower alkyl moiety in a lower alkylsulfonyl group, and the like includes a methyl group, an ethyl group, a propyl group, an isopropyl group, a butyl group, an isobutyl group, a sec-butyl group, a tert-butyl group, a pentyl (or n-amyl) group, an isopentyl group, a tert-pentyl group, a neopentyl group, and the like.

Also, in the definitions of the groups of the general formulae in this specification, the term "the carbon chain may be or is interrupted by at least one oxygen atom" means an ether-type or polyether-type carbon chain in which 1 to 4 oxygen atoms may be or are introduced so that the carbon chain may be or is interrupted at an optional position in carbon chain of the alkanoylamino group, the alkylaminocarbonyl group, the alkanoyloxy group or the alkoxyaminocarbonyl group, and a preferable example of such a group is shown by the formula

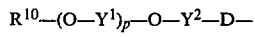

wherein $R^{10}$ represents an alkyl group; $Y^1$ represents a alkylene group having 2 to 6 carbon atoms; p represents 0 or an integer of 1 to 3; $Y^2$ represents a single bond or a alkylene group having 1 to 6 carbon atoms; and D represents a single bond, a carbamid group (—CONH—), a carbamoyl group (—NHCO—), or a carbonyloxy group (—COO—).

The alkyl group or the alkyl moiety of the alkylaminocarbonyl group in this invention is preferably selected from alkyl groups having 1 to 20 carbon atoms and specific examples of the alkyl group are a straight or branched alkyl such as a hexyl group, an isohexyl group, a heptyl group, an isoheptyl group, an octyl group, an isooctyl group, a nonyl group, an isononyl group, a decyl group, an isodecyl group, a undecyl group, an isoundecyl group, a dodecyl group, an isododecyl group, a tridecyl group, an isotridecyl group, a tetradecyl group, an isotetradecyl group, a pentadecyl group, an isopentadecyl group, a hexadecyl group, an isohexadecyl group, a heptadecyl group, an isoheptadecyl group, an octadecyl group, an isootadecyl group, a nonadecyl group, an isononadecyl group, an eicosyl group, an isoeicosyl group, and the like, in addition to the lower alkyl groups described hereinbefore.

The alkylene group in this invention is preferably selected in alkylene groups having 1 to 6 carbon atoms and specific examples of the alkylene group are a lower alkylene group such as a methylene group, an ethylene group, a trimethylene group, a propylene group

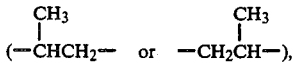

a tetramethylene group, a pentamethylene group, and the like, and also a hexamethylene group, and the like, but the lower alkylene group shown by $Y^1$ is selected in alkylene groups having 2 to 5 carbon atoms.

Also, the alkanoyl group or the alkanoyl moiety of the alkanoylamimo group and the alkanoyloxy group in this invention is preferably selected in the range of 2 to 20 carbon atoms and specific examples of the alkanoyl group are an acetyl group, a propionyl group, a butyryl group, an isobutyryl group, a valeryl group, an isovaleryl group, a pivaloyl group, a hexanoyl group, a heptanoyl group, an octanoyl group, a nonanoyl group, a decanoyl group, a undcanoyl group, a lauroyl group, a tridecanoyl group, a myristoyl group, a pentadecanoyl group, a palmitoyl group, a heptadecanoyl group, a stearoyl group, a nonadecanoyl group, an eicosanoyl group, and the like.

Also, the alkoxy moiety of the alkoxyimino group and the alkoxyaminocarbony group in this invention is preferably selected in the range of 1 to 20 carbon atoms and the specific examples of the alkoxy moiety or group are a methoxy group, an ethoxy group, a propoxy group, an isopropoxy group, a butoxy group, an isobutoxy group, a penytyloxy group, an isopentyloxy group, a hexyloxy group, an isohexyloxy group, a heptyloxy group, an isoheptyloxy group, an octyloxy group, an isooctyloxy group, a nonyloxy group, an isononyloxy group, a decyloxy group, an isodecyloxy group, an undecyloxy group, an isoundecyloxy group, a dodecyloxy group, an isododecyloxy group, a tridecyloxy group, an isotridecyloxy group, a tetradecyloxy group, a pentadecyloxy group, a hexadecyloxy group, a heptadecyloxy group, an octadecyloxy group, a nonadecyloxy group, an eicosyloxy group, and the like.

Thus, the alkanoylamino group, the alkanoyloxy group, the alkylaminocarbonyl group and the alkoxyaminocarbonyl group, the carbon chain of which is interrupted by at least one oxygen atom, is the monooxa-, dioxa, trioxa- or tetraoxa-alkanoylamino group; the monooxa-, dioxa-, trioxa- or tetraoxa-alkanoyloxy group; the monooxa-, dioxa-, trioxa- or tetraoxa-alkylaminocarbonyl group or the monooxa-, dioxa-, trioxa- or tetraoxa-alkoxyaminocarbonyl group formed by the introduction of 1 to 4 oxygen atoms in an optional position of the carbon chain, preferably in the position as shown by $R^{10}$—$(O$—$Y^1)_p$—$O$—$Y^2$—$D$— (wherein $Y^1$, $Y^2$, D and p are the same as defined above) of the above-described specific groups of the alkanoylamino group, the alkanoyloxy group, the alkylaminocarbonyl group or the alkoxyaminocarbonyl group.

The amino acid residue in this invention is a natural or synthetic amino acid in which the hydrogen atom is removed from the amino nitrogen (N end) and the hdyroxy group is removed from the carboxy group (C end) and is practically shown by the formula

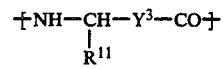

wherein $R^{11}$ represents a hydrogen atom, a lower alkyl group, a hydroxy lower alkyl group, an amino lower alkyl group, a carboxy lower alkyl group, a guanidino lower alkyl group, a lower alkylthio lower alkyl group, a phenyl lower alkyl group, a hydroxyphenyl lower alkyl group, a hydroxyphenoxyphenyl lower alkyl group, an imidazolyl lower alkyl group, or a thienyl group and $Y^3$ represents a single bond or a lower alkylene gorup.

Examples of the particularly preferred amino acid residue are a serine residue (—Ser—), a phenylalanine residue (—Phe—), a β-alanine residue (—β—Ala—), a glutamic acid residue (—Glu—), an aspartic acid residue (—Asp—), a glycine residue (—Gly—), a tyrosine residue (—Tyr—), and the like.

The compounds of this invention constructed by the various combinations of these specific groups include the compounds containing an asymmeteric carbon atom in the molecule and as such a compound, there are various optical isomers. Thus, the compound of this invention includes each isomer separated from the optical isomers and a mixture of these isomers.

Also, some of the compounds of this invention form salts and the invention also includes the pharmaceutically acceptable nontoxic salts of the compounds of foregoing general formula (I). Examples of such salts are salts of alkali metals such as sodium, potassium, and the like; alkaline earth metals such as calcium, magnesium, and the like; bases such as trimethylamine, triethylamine, cyclohexylamine, dicyclohexylamine, diethanolamine, alginine, lysine, and the like; acids such as hydrochloric acid, sulfuric acid, hydrobromic acid, phosphoric acid, formic acid, acetic acid, oxalic acid, succinic acid, fumaric acid, maleic acid, methanesulfonic acid, ethanesulfonic acid, benzenesulfonic acid, and the like; and ammonium salts thereof.

Fatty acid derivatives shown by following general formula (I') and salts thereof are a preferred group of the compounds of this invention.

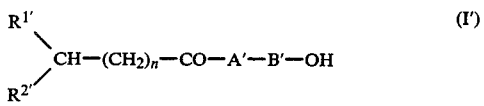

in which
R$^{1'}$, represents a group shown by the formula R$^{10}$—(O—Y$^1$)$_p$—O—Y$^2$—D$^1$ (wherein R$^{10}$, Y$^1$, Y$^2$ and p are the same as defined above, and D$^1$ represents a carbamide group or a carbonyloxy group);
R$^{2'}$ represents an alkyl group having 1 to 20 carbon atoms or a group shown by the formula R$^{10}$—(O—Y$^1$)$_p$—O—Y$^2$—D$^2$— (wherein R$^{10}$, Y$^1$, Y$^2$ and p are the same as defined above and D$^2$ represents a carbamoyl group (—NHCO—));
n represents an integer of 1 to 3; and
A' and B', which may be the same or different, each represents a single bond or an amino acid residue selected from the group consisting of a serine residue, a phenylalanine residue, a β-alanine residue, a glutamic acid residue, an aspartic acid residue, a glycine residue, and a tyrosine residue.

The particularly preferred compounds in the foregoing fatty acid derivatives are as follows:
N-[3-(3,6-dioxahexanoyloxy)octadecanoyl]-L-phenylalanine.
N-[3-(3,6-dioxahexanoyloxy)octadecanoyl]-L-serine.
N-[3-(3,6,9-trioxapentadecanoyloxy)octadecanoyl]-L-phenylalanine.
N-[3-(3,6,9,12-tetraoxahexadecanoyloxy)octadcanoyl]-L-phenylanine.
(S)-3-(3,6-dioxahexadecanamido)-3-(3-oxatridecylcarbamoyl)propionic acid.

The compounds shown by the above-described general formula (I) and the salts thereof can be prepared by various processes.

Thus, the invention also provides processes of producing the compounds shown by general formula (I) and the salts thereof of this invention. That is, the compounds of general formula (I) and the salts thereof of this invention can be produced by processes A to D as described hereinafter.

Process A (Release of the protection group for the carboxy group):

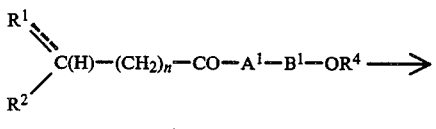

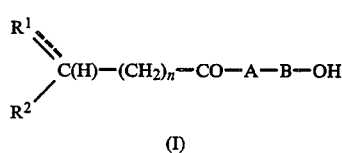

wherein R$^1$, R$^2$, ===, (H), n, A, and B are the same as described above; A$^1$ and B$^1$, which may be the same or different, each represents a single bond or an amino acid residue which may be protected; and R$^4$ represents a protective group for the carboxy group.

As shown above, the compounds of this invention shown by general formula (I) can be produced by releasing the protective group from the corresponding compound having the protective group shown by general formula (II).

In this case, the protective group for the amino acid residue of A$^1$ or B$^1$ and the protective group for the carboxy group shown by R$^4$ are selected from the groups which are widely used in the field of the peptide chemistry, and which are a protective group for the amino group, the carboxy group, and/or the hydroxy group in the production step of the compounds of this invention, and which can be easily released under a mild reaction condition.

Examples of such a protective group for the amino group are acyl groups such as a t-butoxycarbonyl group, a benzyloxycarbonyl group, a p-methoxybenzyloxycarbonyl group, a cyclohexanecarbonyl group, a phthaloyl group, a trifluoroacetyl group, and the like, and aralkyl groups such as a benzhydryl group, a trytyl group, and the like. Examples of the protective group for the carboxy group are ester residues for forming a methyl ester, an ethyl ester, a propyl ester, a butyl ester, a t-butyl ester, an acetoxymethyl ester, a pivaloylmethyl ester, a benzylcarbonyloxymethyl ester, a benzoyloxymethyl ester, a phthalidyl ester, a 5-oxo-2-tetrahydrofuryl ester, a benzyl ester, a p-nitrobenzyl ester, a benzhydryl ester, a trityl ester, a phenyl ester, etc. Also, examples of the protective group for the hydroxy group are acyl groups such as an acetyl group, a propionyl group, a butyryl group, a valeryl group, etc., and aralkyl groups such as a benzyl group, a benzhydryl group, a trityl group, and the like.

The releasing reaction of the ester residue as the protective group for the carboxy group is properly selected from the methods widely used in the field of the peptide chemistry according to the kind of the starting material for use, particularly the ester residue. As such a reactions, there are hydrolysis by an acid catalyst, saponification under a basic condition, and the releasing reaction of the ester residue by a catalytic reduction or a chemical reduction.

For example, when the ester residue is a tert-butyl group or a benzhydryl group, it is simple and suitable to dissolve a starting material shown by general formula (II) in a solvent such as trifluoroacetic acid, a mixture of trifluoroacetic acid and anisole, a mixture of hydrobromic acid and acetic acid, a mixture of hydrochloric acid and dioxane, and the like, and treating the solution under cooling or at room temperature.

Also, when the ester residue is a lower alkyl group such as a methyl group, an ethyl group, and the like, it is proper to dissolve a starting material shown by general formula (II) in a solvent such as methanol, ethanol, and the like, and performing the saponification thereof in the presence of a base such as sodium hydroxide, potassium hydroxide, and the like, under heating.

Furthermore, when the ester residue is a benzyl group, a benzhydryl group, a p-nirtobenzyl group, and the like, the ester group can be easily released by a catalytic reduction using palladium carbon, and the like, as the catalyst.

In addition, when the amino acid residue shown by A$^1$ and B$^1$ of general formula (II) is an amino acid residue having a carboxy group substituted by an ester residue, these ester residues may be simultaneously released or a desired ester residue only may be selectively released according to purposes.

Also, when the amino acid residue shown by $A^1$ and/or $B^1$ has a protective group for the amino group or a protective group for the hydroxy group, the release of the protective group can be performed by a method which is ordinarily used in the field of the peptide chemistry. For example, the release of a protective group for the amino group in the case of using an aralkyl group such as a trityl group, and the like, or various acyl groups as described above can be easily performed by a hydrolysis using an acid. In such a case, formic acid, trifluoroacetic acid, hydrochloric acid, and the like, is preferably used as the acid.

Furthermore, in the case of using, for example, a benzyl group as a protective group for the hydroxy group, a catalytic reduction using palladium-carbon as the catalyst can be employed for releasing the protective group.

In addition, the release of the protective groups for the carboxy group, for the hydroxy group and/or for the amino group can be simultaneously performed.

Process B (Amide-formation process):

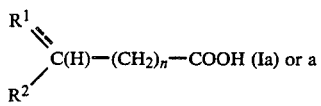

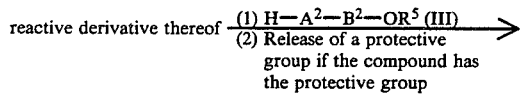

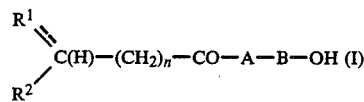

wherein $R^1$, $R^2$, ===, (H), A, B, and n are the same as defined above with proviso that A and B are not a single bond at the same time; $R^5$ represents a hydrogen atom or a protective group for the carboxy group as defined in above part concerning $R^4$; and one of $A^2$ and $B^2$ represents an amino acid residue which may have one or more protective groups and the other represents a single bond or an amino acid residue which may have one or more protective groups.

The compound of this invention shown by general formula (I) can be produced by reacting the carboxylic acid shown by general formula (Ia) or the reactive derivative thereof and the amino acid or the peptide shown by general formula (III).

As the reactive derivative of the compound shown by general formula (Ia), there are acid halides such as acid chloride, acid bromide, and the like; acid azide; active esters such as the ester with N-hydroxybenzotriazole, the ester with N-hydroxysuccinimide, the p-nitrophenyl ester, and the like; symmeteric acid anhydrides; alkyl carbonate mixed acid anhydrides; mixed acid anhydrides with p-toluenesulfonic acid, and the like.

It is advantageous to perform the amide-forming reaction using the compound of general formula (Ia) or the reactive derivative thereof and an almost equimolar amount or slightly excessive or deficient amount of the compound of formula (III) in an organic solvent inactive to the reaction under cooling or at room temperature. The solvent is properly selected according to the kind of the starting material to be used and as such a solvent, tetrahydrofuan, dioxane, ether, benzene, toluene, xylene, methylene chloride, dichloroethane, chloroform, carbon tetrachloride, dimethylformamide, ethyl acetate, acetonitrile, etc., are usually used.

When the compound of general formula (Ia) is reacted in the form of the free carboxylic acid, it is advantageous to perform the reaction in the presence of a condensing agent such as N,N'-dicyclohexylcarbodiimide, 1,1-carbonylimidazole, and the like.

It is sometimes advantageous for smoothly progressing the reaction to perform the reaction in the presence of a tertiary base such as triethylamine, pyridine, picoline, lutidine, N,N-dimethylaniline, and the like, or an inorganic base such as potassium carbonate, sodium carbonate, sodium hydroxide, and the like, and thus, the mode of the reaction is employed on considering the kind of the starting material to be used.

When the active ester is used as the reactive derivative of the compound shown by formula (Ia), the amide compound can be obtained even when the carboxy group of the compound of formula (III) is not substituted by the ester residue and thus, $R^5$ of the compound of general formula (III) may be a hydrogen atom.

Then, when the amide compound thus formed has one or more protective groups, the protective groups are released by the same manner as in Process A.

Process C (Amide formation process):

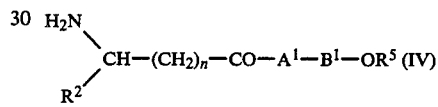

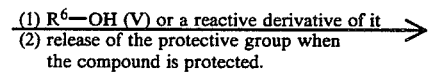

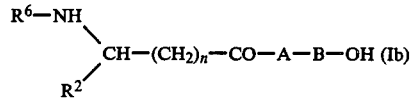

wherein $R^2$, $R^5$, $A^1$, $B^1$, A, B, and n are the same as defined above and $R^6$ represents an alkanoyl group the carbon chain of which may be interrupted by at least one oxygen atom or a group shown by $R^3$—(N—H—Y—CO)$_m$— (wherein $R^3$, Y and m are the same as defined above).

The amide compound shown by general formula (Ib) is produced by reacting the amine compound shown by general formula (IV) and the carboxylic acid shown by general formula (V) or a reactive derivative thereof.

The kind of the solvent in this reaction, the amount of the starting material, and the like, and the reaction conditions such as the reaction temperature, and the like, are the same as those in Process B.

Process D (Amide-formation process):

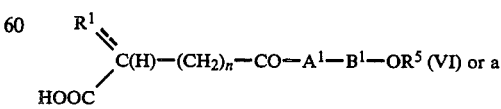

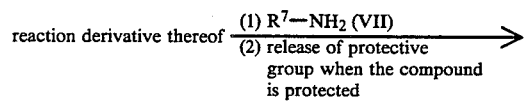

-continued

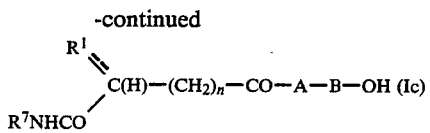

wherein $R^1$, $R^5$, $A^1$, $B^1$, A, B, ≡, (H), and n are the same as defined above and $R^7$ represents an alkyl group the carbon chain of which may be interrupted by at least one oxygen atom or an alkoxy group the carbon chain of which is interrupted by at least one oxygen atom.

The compound of this invention shown by general formula (Ic) is produced by reacting the carboxylic acid shown by general formula (VI) or a reactive derivative thereof and the amine shown by general formula (VII).

The reaction conditions, and the like, for the amide formation are completely the same as those in Process B and Process C.

Process E (Esterification):

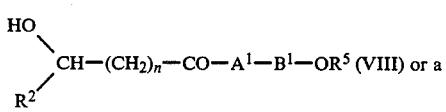

reactive derivative thereof $\xrightarrow[\substack{\text{(2) release of the protective} \\ \text{group when the compound} \\ \text{is protected}}]{\text{(1) } R^8\text{—OH (IX) or a reactive derivative of it}}$

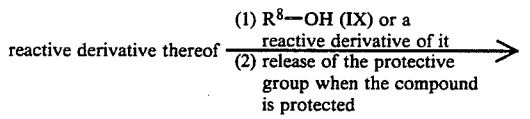

wherein $R^2$, $R^5$, $A^1$, $B^1$, A, B, and n are the same as defined above and $R^8$ represents an alkanoyl group the carbon chain of which is interrupted by at least one oxygen atom or the group shown by $R^3$—(N-H—Y—CO)$_m$— (wherein $R^3$, Y and m are the same as defined above.

The compound of this invention shown by general formula (Id) is produced by reacting the alcohol shown by general formula (VIII) or a reactive derivative thereof and the carboxylic acid shown by general formula (IX) or a reactive derivative thereof.

The reaction is a general ester-forming reaction and can be performed by an ordinary method. However, a method of reacting the compound of general formula (VIII) and the compound of general formula (IX) in the presence of a condensing agent such as dicyclohexylcarbodiimide, and the like is advantageous. It is suitable to react the compound of general formul (VIII) and a equimolar or slightly excessive or deficient amount of the compound of formula (IX) in an organic solvent inactive to the reaction, such as dimethylformamide, methylene chloride, etc., at room temperature or under heating. At the reaction, it is sometimes advantageous for the smooth progress of the reaction to add a base such as dimethylaminopyridine to the reaction system.

Also, the reaction can be performed by an ordinary method using an acid halide, an acid anhydride, and the like, as the reactive derivative of the acid component or a halogen substitution product or a tosylate derivative, etc. shown by the general formula

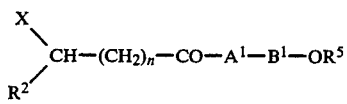

(wherein $R^2$, $R^5$, $A^1$, $B^1$ and n are the same as above and X represents a halogen atom or a toluenesulfonyloxy group), as a reactive derivative of the alcohol component. In addition, specific examples of the halogen atom shown by X are a chlorine atom, a bromine atom, and the like.

Process F (Alkoxyimino-formation):

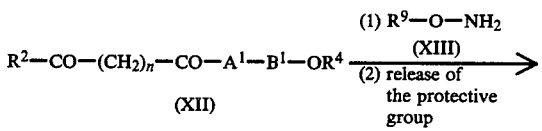

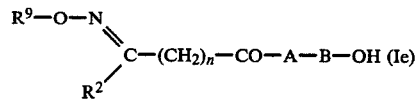

wherein $R^2$, $R^4$, $A^1$, $B^1$, A, B and n are the same as defined above and $R^9$ represents an alkyl group.

The substituted oxyiminoalkane acid derivative shown by general formula (Ie) is produced by the reaction of the ketocarboxylic acid derivative shown by general formula (XII) and the substituted hydroxylamine shown by general formula (XIII) and then releasing the protective group.

The reaction proceeds in non-solvent but is usually performed in an organic solvent such as methanol, ethanol isopropanol, benzene, toluene, xylene, and the like under cooling, at room temperature, or under heating. Also, the releasing reaction of the protective group in the 2nd step is completely the same as that in Process A and the reaction conditions are properly selected according to the kind of the starting material, in particular, the ester residue.

The compounds of this invention thus produced by the various processes as described above are isolated and purified as they are or as the salts thereof. The isolation and purification of these compounds are performed by the manners ordinary used in the field of the art, such as crystallization, distillation, extraction, various chroamtographies, recrystallization, and the like.

The compound of foregoing general formula (I) and the salt thereof provided by the present invention has a structural feature in the point that the fatty acid moiety thereof

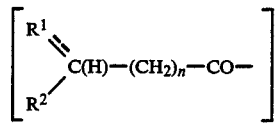

has a carbamide group, a carbamoyl group, an ether-type or polyether-type group (preferably, the group shown by $R^{10}$—(O—$Y^1$)p—O—$Y^2$—D—, or an alkoxyimino group, has a markedly excellent fibrinolytic action as compared to known acylpeptides, and are useful for the prophylaxis and treatment of various thrombotic diseases, such as peripheral arteriovenous occlusion, pulmonary embolism, coronary occlusion, cerebral infarction, myocardial infarction, retinal arteriovenous occlusion, cancer, and the like.

In particular, the compounds of this invention have been discovered after investigating the point of water solubility, which has never been attained in known acylpeptides. That is, the compounds of this invention have very improved water solubility, whereby sufficient pharmacological effect of the compounds can be expected and also the preparations of the compounds, such as the application to injections, and the like, can be easily performed. For example, the solubility of compound of Example 21 is more than 5 mg/ml saline.

The pharmacological actions or effects of the compounds of this invention were confirmed by the following methods.

FIBRINOLYTIC ACTION (Fibrin-clot lysis assay)

Experimental Procedure:

Fibrinogen (1 mg/50 μl, made by Green Cross Corporation) and various amounts of the test compounds, were added to test tubes, followed to make a total volume of 850 μl with cold Tris-buffered saline (20 mM Tris-buffer, pH 7.4, containing 140 mM NaCl). To the solutions were added 100 μl of Urokinase solution (30 CTA unit/0.1 ml) and 50 μl of thrombin solution (2 NIH units/50 μl) to make final clot volume of 1 ml each in test tubes in an ice bath. The tubes were quickly shaken to mix the reagents well and immediately placed in a 37° C. water bath, and the clot lysis time was recorded. Test compounds were dissolved in physiological saline, except contrast one dissolved in physiological saline containing 10% cremophore and 0.15% ethanol. Thus, by measuring the time of clot lysis, the relative activity of the fibrinolytic action of the test compound to that of Urokinase using the system of Urokinase alone as the control was determined. The results of the pharmacological effect of the compounds of this invention are shown in Table 1 below together with that of 3-hexadecanoyloctadecanoyl-β-alanyl-L-phenylalanine having the formula

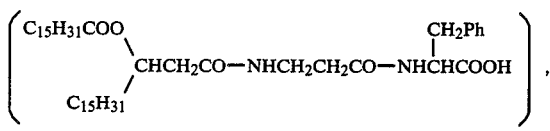

which is one of the compounds having the most excellent fibrinolytic action in known compounds.

Experimental Result:

TABLE 1

| Example No. | Fibrinolytic Action* | Solvent |
|---|---|---|
| 14 | Maximum + 150% at $1 \times 10^{-5}$ M | Physiological saline solution |
| 19 | Maximum + 130-140% at $1 \times 10^{-5}$ M | Physiological saline solution |
| 20 | Maximum + 130-150% at $1 \times 10^{-5}$ M | Physiological saline solution |
| 21 | Maximum + 150-160% at $3 \times 10^{-6}$ M | Physiological saline solution |
| 22 | Maximum + 160% at $3 \times 10^{-5}$ M | Physiological saline solution |
| Known compound | Maximum + 140-150% at $1 \times 10^{-4}$ M | Cremophore solution |

*Relative activity (%) with the activity of Urokinase alone being defined to 100%.

In addition, the acute toxicity of the compound in Example 21 was measured as follows. That is, a physiological saline solution of 5 mg/ml of the compound was injected to the veins of the tails of mice at a rate of 0.2 ml/min. and the mice were observed for one week but no dead mice were observed. The toxicity is higher than 200 mg/40 ml saline/kg (iv) of mouse, which shows that the compound has almost no toxicity.

The preparations containing the compound of general formula (I) or the salts thereof as the component can be produced by applying the means conventionally used, using carriers for preparation, excipients, and the like usually used in the field of the art. The medicament can be administered orally as tablets, pills, capsules, granules, powders, liquids, and the like, or may be administered by intravenous injection, intramuscular injection, and the like, or further may be parenterally administered as suppositories, and the like.

The dose of the compound can be properly determined for each patient according to the symptom, the age and sex of the patient, etc., but are ususally 5–500 mg/kg, preferably 10–100 mg/kg per day per adult in the case of intravenous injection and are usually 5–5000 mg/kg, preferably 10–1000 mg/kg per day per adult in the case of oral administration, the medicament is administered in one time or 2–4 times.

Then, the present invention will be further explained by the following examples.

Symbols which are used in examples have following meanings respectively.
Bzl: benzyl group,
BOC: t-butoxycarbonyl group,
Bu: butyl group,
t-Bu: t-butyl group,
HOBT: N-hydroxybenzotriazole
HOSU: N-hydroxysuccinimide
DCC: dicyclohexylcarbodiimide
TFA: trifluoroacetic acid
TsOH: p-toluenesulfonic acid
TEA: triethylamine
DMF: dimethylformamide
DMAP: 4-dimethylaminopyridine
Pd-C: palladium-carbon

EXAMPLE 1

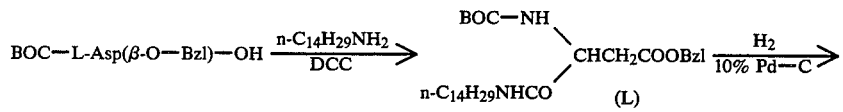

-continued

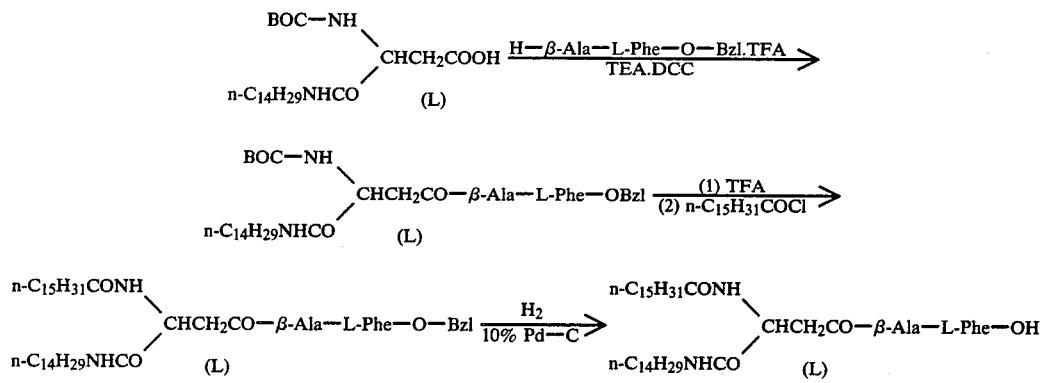

(i) In 50 ml of methylene chloride was dissolved 10 g of t-butoxycarbonyl-L-aspartic acid benzyl ester and after cooling the solution to 0° C. and adding thereto 6.6 g of tetradecylamine and 6.4 g of DCC, the mixture was stirred for 2 hours at 0° C. and further for 2 days at room temperature. Precipitates thus formed were removed by filtration and the filtrate was washed with a saline solution, cooled dil. hydrochloric acid, a saline solution, 4% an aqueous sodium hydrogen carbonate solution and a saline solution successively, and then was dried with anhydrous magnesium sulfate. The solvent in the solution thus obtained was distilled off under reduced pressure and 10.22 g of a white solid material was obtained. The material was dissolved in 130 ml of ethyl acetate and after removing insoluble matters by filtration, the solvent in the filtrate was distilled away under reduced pressure to provide 9.66 g of a white powder of L-3-t-butoxycarboamido-3-tetradecylcarbamoylpropionic acid benzyl ester.

IR(KBr) 3310, 2910, 2830, 1730, 1655 cm$^{-1}$.

NMR(CDCl$_3$, δ) 0.90(3H, t, J=6 Hz), 1.1~2.0(33H, m), 2.88(2H, dq, J=11 Hz, 7 Hz, 6 Hz), 3.2(2H, m), 4.5(1H, m), 5.14(2H, s), 5.64(1H, m), 6.44(1H, m), 7.36(5H, s).

(ii) 5.2 g of the product obtained as above was dissolved in a mixture of 50 ml of ethyl acetate and 50 ml of methanol and after adding thereto 500 mg of Pd-C, the product was hydrogenated under normal pressure at room temperature. The reaction mixture was filtered and the solvent in the filtrate was distilled off under reduced pressure to provide 4.15 g of a white solid material of L-3-t-butoxycarboamido-3-tetradecylcarbamoylpropionic acid.

NMR(CDCl$_3$, δ) 0.88(3H, t, J=6 Hz), 1.1~2.0(33H, m), 2.96(2H, m), 3.24(2H, m), 4.48(1H, m), 5.8(1H, m), 6.7(1H, m).

(iii) In 10 ml of methylenechloride were dissolved 1.59 g of the product obtained in the above (i) and 1.65 g of β-alanyl-L-phenylalanine benzyl ester TFA salt and after cooling the solution to 0° C. and adding 521 μl of TEA and 772 mg of DCC, the mixture was stirred for 1 hour at 0° C., and furter for 24 hours at room temperature.

Precipitates thus formed was removed by filtration, and the filtrate was washed with a saline solution, cooled dil. hydrochloric acid, a saline solution, 4% sodium hydrogencarbonate water solution and a saline solution succesively, and was dried over anhydrous magnesium sulfate. The solvent in the solution obtained was distilled away to provide 1.92 g of a white solid material of N-(L-3-t-butoxycarboamido-3-tetradecylcarbamoylpropionyl-β-alanyl-L-phenylalanine benzyl ester.

IR(KBr) 3290, 2910, 2830, 1730, 1680, 1635 cm$^{-1}$.

NMR(CDCl$_3$, δ) 0.86(3H, t, J=6 Hz), 1.1~2.0(33H, m), 2.1~2.2(2H, m), 2.6(2H, m), 3.0~3.3(4H, m), 4.4(1H, m), 4.86(1H, m), 5.2(2H, s), 6.76~7.60(3H, m), 7.24(5H, s), 7.36(5H, s).

(iv) In a mixture of 20 ml of methylenechloride and 20 ml of anisole was dissolved 1.9 g of the product obtained in the above (iii) and after cooling the solution to −10° C. and adding dropwise 40 ml of TFA, the mixture was stirred for 2 hours at 0° C. The reaction mixture was concentrated under reduced pressure. Benzene was added to the residue and the formed mixture was concentrated under reduced pressure, which was conducted twice. The residue was dissolved in 30 ml of methylenechloride and after cooling the mixture to 0° C. and adding thereto 824 μl of TEA, and then cooling the mixture to −20° C., a solution of 714 mg of hexadecanoyl chloride in 10 ml of methylenechloride) was added to the mixture. The mixture was stirred for 1 hour at 0° C. The reaction mixture was washed with a saline solution, dil. hydrochloric acid and a saline solution succesively and dried over anhydrous magnesium sulfate. The drying agent is removed by filtration, and the filtrate is distilled under reduced pressure to remove the solvent.

790 mg of a white powder of N-[(S)-3-tetradecylcarbamoyl-3-hexadecaneamidopropionyl]-alanyl-L-phenylalanine benzyl ester was obtained.

IR(KBr) 3280, 2910, 2830, 1735, 1635 cm$^{-1}$.

NMR(CDCl$_3$, δ) 0.88(6H, t, J=6 Hz), 1.1~1.8(50H, m), 2.16~2.8(6H, m), 3.0~3.34(6H, m), 4.8(2H, m), 5.2(2H, s), 7.30(5H, s), 7.38(5H, s)

(v) In a mixture of 200 ml of dioxane and 50 ml of methanol was suspended 750 mg of the product obtained in the above (iv) and after adding thereto 150 mg of 10% Pd-C, the product was hydrogenated under normal pressure at room temperature. The reaction mixture was filtered and the filtrate was concentrated under reduced pressure and the residue formed was subjected to column chromatography (silica gel: 100 g; chloroform-methanol: from 20:1 to 5:1) to purify the product. 600 mg of a white powder of N-[((S)-3-hexadecaneamido-3-tetradecylcarbamoylpropionyl)-β-alanyl-L-phenylalanine was obtained.

IR(KBr) 3275, 2910, 2830, 1715, 1635, 1540 cm$^{-1}$.
mp 190°–193° C.

NMR(CDCl$_3$+CD$_3$OD, δ) 0.87(6H, t, J=6 Hz), 1.1~1.7(50H, m), 2.10~2.65(6H, m), 3.0~3.3(6H, m), 4.7(2H, m), 7.26(5H, s).

EXAMPLE 2

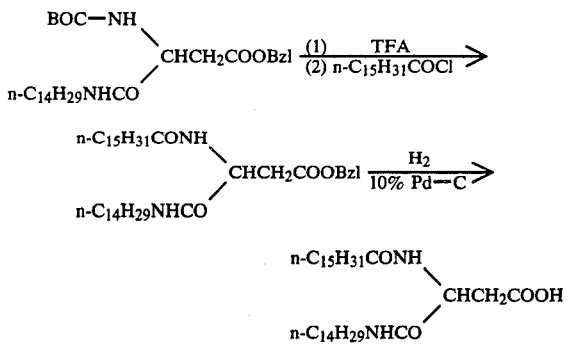

(i) By following the same procedure as in Example 1-(iv) using 1.5 of the product obtained in the above Example 1-(i), 1.86 g of a white powder of L-3-hexadecaneamido-3-tetradecylcarbamoylpropionic acid benzyl ester was obtained.

IR(KBr) 3275, 2910, 2830, 1730, 1635, 1440 cm$^{-1}$.

NMR(CDCl$_3$, δ) 0.86(6H, t, J=6 Hz), 1.1~1.7(50H, m), 2.2(2H, t, J=8 Hz), 2.82(2H, dq, J=18 Hz, 8 Hz, 5 Hz), 3.18(2H, q, J=6 Hz), 4.78(1H, m), 5.16(2H, s), 6.54(1H, m), 6.78(1H, d, J=9 Hz), 7.38(5H, s).

(ii) By following the same procedure as in Example 1-(v) using 1 g of the product obtained in the above (i), 800 mg of a white powder of L-3-hexadecaneamido-3-tetradecylcarbamoylpropionic acid was obtained.

mp. 113°-115° C.

IR(KBr) 3275, 2910, 2830, 1720, 1620 cm$^{-1}$.

NMR(CDCl$_3$+CD$_3$OD) 0.88(6H, t, J=6 Hz), 1.1~1.8(50H, m), 2.22(2H, t, J=9 Hz), 2.72(2H, d, J=8 Hz), 3.05~3.30(2H, m), 4.72(1H, t, J=8 Hz).

EXAMPLE 3

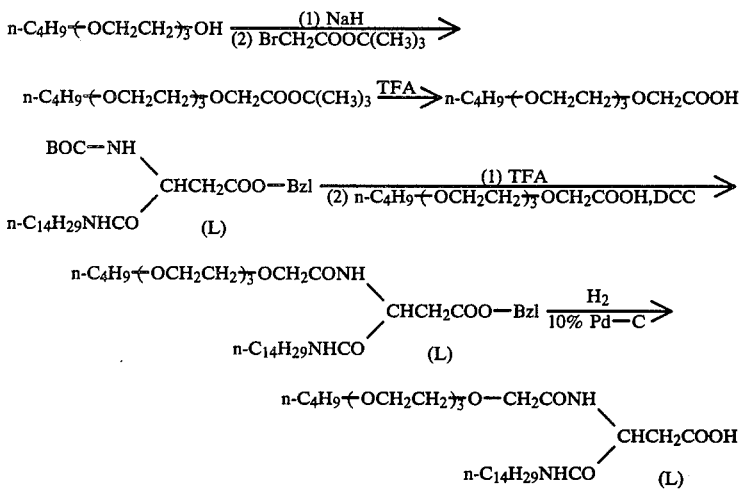

(i) In 50 ml of DMF was dissolved 16.48 g of triethyleneglycol monobutyl ether and after cooling the solution to 0° C. and adding 3.3 g of sodium hydride (60% oil solution), the reaction mixture was stirred for 30 minutes at room temperature. The reaction mixture was added dropwise to another solution which was obtained by dissolving 15.6 g of bromoacetic acid t-butyl ester in 50 ml of DMF and cooling the solution to −10° C. After stirring the mixture for 1 hour at −5° C., for 1 hour at 0° C. and for 30 minutes at room temperature, the reaction mixture was distilled under reduced pressure to remove the solvent. Water and ethyl acetate was added to the formed residue to separate the product, and the ethyl acetate layer separated was washed with water, dried over anhydrous magnesium sulfate, and concentrated under reduce pressure to provide 21 g of an oily product. The product was subjected to column chromatography (silica gel:200 g; hexane-ethyl acetate=4:1) to purify the product. 8.6 g of a colorless oily material of 3,6,9,12-tetraoxahexadecanoic acid t-butyl ester was obtained.

NMR(CDCl$_3$, δ) 0.85(3H, t, J=6 Hz), 1.1~1.7(13H, m), 3.43(2H, t, J=6 Hz), 3.5~3.75(12H, m), 3.96(2H, s).

(ii) To the product obtained in the above (i) was added dropwise 85 ml of TFA while cooling to 0° C. and after stirring the mixtuer for 1 hour at room temperature, the reaction mixture was concentrated under reduced pressure. The residue thus formed was subjected to column chromatography (silica gel: 200 g; chloroformmethanol=20:1) to purify the product. 6.4 g of a colorless oily material of 3,6,9,12-tetraoxahexadecanoic acid was obtained.

NMR(CDCl$_3$, δ) 0.8~1.1(3H, m), 1.2~1.7(4H, m), 3.45(2H, J=6 Hz), 3.65(12H, t, J=3 Hz), 4.13(2H, s).

(iii) In a mixture of 20 ml of methylenechloride and 20 ml of anisole was dissolved 3 g of the product obtained in the above 1-(i) and after cooling the solution to −20° C. and adding dropwise thereto 60 ml of TFA, the mixture was stirred for 1 hour at 0° C. The reaction mixture was concentrated under reduced pressure. To the residue was added benzene and the mixture was concentrated under reduced pressure, which was conducted twice. The product was dried using high vacuum pump. The residue formed was dissolved in 20 ml of methylenechloride and after cooling the solution to 5°-10° C. and adding thereto a solution of 1.53 g of the product obtained in the above (ii) in 10 ml of methylenechloride, cooling the mixture to 0° C. and adding 0.9 ml of TEA and 1.32 g of DCC, the reaction mixture was stirred for 3 days at room temperature. Precipitates thus formed were removed by filtration and the filtrate was washed with cooled dil. hydrochloric acid, a saline solution, 4% sodium hydrogencarbonate water solution and a saline solution successively, dried over anhydrous magnesium sulfate, and concentrated under reduced pressure to provide 3.6 g of an oily material. The oily material was subjected to column chromatography (silica gel: 150 g; chloroform:methanol=from 100:1 to 50:1) to purify the product. 2.17 g of a colorless oily material of L-3-tetradecylcarbamoyl-3-(3,6,9,12-tetraoxahexadecaneamido)propionic acid benzyl ester.

IR(neat) 3290, 2910, 2840, 1730, 1655 cm$^{-1}$.

NMR(CDCl$_3$, δ) 0.8~1.0(6H, m), 1.2~1.7(28H, m), 2.84~2.96(2H, m), 3.2(2H, m), 3.45(2H, t, J=6 Hz), 3.6~3.8(12H, m), 4.04(2H, s), 4.86(1H, m), 5.16(2H, s), 6.58(1H, m), 7.36(5H, s), 7.78(2H, d, J=9 Hz).

(iv) By following the same procedure as in Example 1-(ii) using 2.1 g of the product obtained in the above (iii), 1.8 g of colorless waxy solid material of L-3-tetradecylcarbamoyl-3-(3,6,9,12-tetraoxahexadecaneamido)propionic acid was obtained.

IR(KBr) 3280, 2910, 2830, 1725, 1650 cm$^{-1}$.

NMR(CDCl$_3$, δ) 0.8~1.0(6H, m), 1.16~1.70(28H, m), 2.88(2H, t, J=7 Hz), 3.2(2H, m), 3.49(2H, t, J=7 Hz), 3.6~3.8(12H, m), 4.06(2H, s), 4.82(1H, m), 6.6~7.0(2H, m), 7.89(1H, d, J=9 Hz).

EXAMPLE 4 n-C$_4$H$_9$(OCH$_2$CH$_2$)$_3$OCH$_2$CONH\
\\
CHCH$_2$COOH + H—L-Phe—OBzl.TβOH $\xrightarrow{\text{DCC}}$
/
n-C$_{14}$H$_{29}$NHCO   (L)

n-C$_4$H$_9$(OCH$_2$CH$_2$)$_3$OCH$_2$CONH\
\\
CHCH$_2$CO—L-Phe—OBzl $\xrightarrow[10\%\ \text{Pd—C}]{\text{H}_2}$
/
n-C$_{14}$H$_{29}$NHCO   (L)

n-C$_4$H$_9$(OCH$_2$CH$_2$)$_3$OCH$_2$CONH\
\\
CHCH$_2$CO—L-Phe—OH
/
n-C$_{14}$H$_{29}$NHCO   (L)

(i) By following the same procedure as in Example 1-(iii) using the 1.16 g of the product obtained in Example 3 and 881 mg of L-phenylalanine benzyl ester TsOH salt, 1.4 g of a viscous material of N-[L-3-tetradecylcarbamoyl-3-(3,6,9,12-tetraoxahexadecanamido)propinyl]-L-phenylalanine benzylester was obtained.

IR(neat) 3270, 2910, 2840, 1725, 1635 cm$^{-1}$.

NMR(CDCl$_3$, δ) 0.8~1.0(6H, m), 1.16~1.70(28H, m), 2.72(2H, m), 3.04~3.25(4H, m), 3.45(2H, t, J=7 Hz), 3.55~3.8(12H, m), 4.03(2H, s), 4.6~5.0(2H, m), 5.12(2H, s), 6.57(1H, d, J=9 Hz), 6.86(1H, m), 7.0~7.46(10H, m), 7.98(1H, d, J=9 Hz).

(ii) By following the same procedure as in Example 1-(ii) using the 1.4 g of the product obtained in the above (i), 1 g of a waxy solid material of N-[3-tetradecylcarbamoyl-3-(3,6,9,12-tetraoxahexadecanamido)propionyl]-L-phenylalanine was obtained.

IR(KBr) 3275, 2910, 2830, 1720, 1630 cm$^{-1}$.

NMR(CDCl$_3$, δ) 0.8~1.0(6H, m), 1.1~1.7(28H, m), 2.70(2H, t, J=7 Hz), 3.0~3.3(4H, m), 3.46(2H, t, J=7 Hz), 3.5~3.96(12H, m), 4.02(2H, s), 4.70(2H, m), 6.65(1H, m), 7.04(1H, m), 7.22(5H, s), 7.99(1H, d, J=9 Hz).

EXAMPLE 5

BOC—NH\
\\
CH(CH$_2$)$_2$COO Bzl + n-C$_{12}$H$_{25}$NH$_2$ $\xrightarrow{\text{DCC}}$
/
HOOC   (L)

BOC—NH\
\\
CH(CH$_2$)COO Bzl $\xrightarrow[\text{(2) n-C}_4\text{H}_9\text{(OCH}_2\text{CH}_2\text{)}_3\text{OCH}_2\text{COOH,DCC}]{\text{(1) TFA}}$
/
n-C$_{12}$H$_{25}$NHCO   (L)

n-C$_4$H$_9$(OCH$_2$CH$_2$)$_3$OCH$_2$CONH\
\\
CH(CH$_2$)$_2$COO—Bzl $\xrightarrow[10\%\ \text{Pd—C}]{\text{H}_2}$
/
n-C$_{12}$H$_{25}$NHCO   (L)

n-C$_4$H$_9$(OCH$_2$CH$_2$)$_3$OCH$_2$CONH\
\\
CH(CH$_2$)$_2$COOH
/
n-C$_{12}$H$_{25}$NHCO   (L)

(i) By following the same procedure as in Example 1-(i) using 10 g of N-t-butoxycarbonyl-L-glutamic acid benzyl ester and 5.5 g of n-decylamine, 2.4 g of a powder of L-4-t-butoxycarboamido-4-dodecylcarbamoyl butyric acid benzyl ester was obtained.

IR(KBr) 3300, 2900, 2830, 1725, 1675, 1645 cm$^{-1}$.

NMR(CDCl$_3$, δ) 0.84(3H, t, J=6 Hz), 1.1~1.6(29H, m), 2.0(2H, m), 2.5(2H, m), 3.23(2H, q, J=7 Hz), 4.12(1H, m), 5.15(2H, m), 5.27(1H, d, J=9 Hz), 6.2(1H, m), 7.37(5H, m).

(ii) By following the same procedure as in Example 3-(iii) using 2.42 g of the product obtained in the above (i) and 1.27 g of 3,6,9,12-tetraoxahexanoic acid, 1.5 g of a colorless oily material of L-4-dodecylcarbamoyl-4-(3,6,9,12-tetraoxahexanamido)butyric acid benzyl ester was obtained.

IR(KBr) 3275, 2910, 2830, 1730, 1650 cm$^{-1}$.

NMR(CDCl$_3$, δ) 0.8–1.0(6H, m), 1.15~1.70(24H, m), 2.0~2.25(2H, m), 2.4~2.6(2H, m), 3.22(2H, q, J=7 Hz), 3.46(2H, t, J=7 Hz), 3.55~3.74(12H, m), 4.02(2H, s), 4.47(1H, m), 5.14(2H, s), 6.34(1H, m), 7.36(5H, s), 7.47(1H, d, J=10 Hz).

(iii) By following the same procedure as in Example 1-(ii) using 1.4 g of the product obtained in the above -(i), 1.1 g of a white powder of L-4-dodecylcarbamoyl-4-(3,6,9,12-tetraoxahexanamido)butyric acid was obtained.

IR(KBr) 3350 (broad), 2920, 2840, 1720, 1650 cm$^{-1}$.

NMR(CDCl$_3$, δ) 0.8~1.0(6H, m), 1.06~1.70(24H, m), 1.92~2.12(2H, m), 2.18~2.56(2H, m), 3.22(2H, q, J=7 Hz), 3.47(2H, t, J=7 Hz), 3.55~3.75(12H, m), 4.03(2H, s), 4.64(1H, m), 7.03(1H, t, J=7 Hz), 7.62(1H, d, J=10 Hz).

EXAMPLE 6

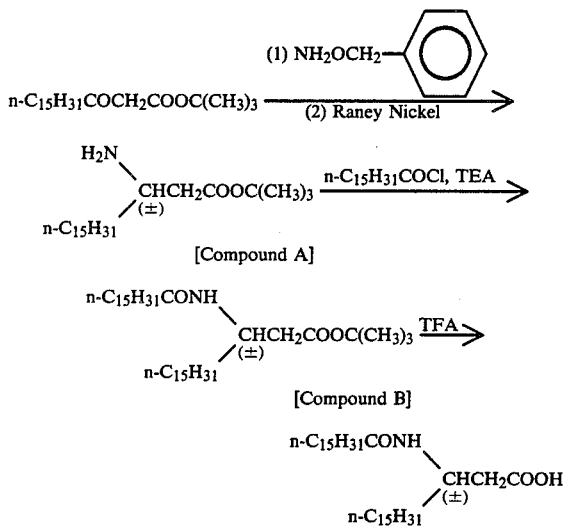

(i) In 300 ml of methanol was dissolved 10 g of β-ketooctadecanoic acid t-butyl ester and after adding thereto 4.6 g of O-benzylhydroxylamine hydrochloride and 3.9 ml of TEA, the mixture was refluxed for 1 hour. The mixture was distilled to remove methanol. The residue was dissolved in methylenechloride. The methylenechloride solution thus obtained was washed with cooled dil. hydrochloric acid solution, dried over anhydrous magnesium sulfate, and distilled under reduced pressure to remove the solvent. 12.8 g of a pale yellow oily material was obtained. The material was dissolved in 100 ml of methanol. To the solution was added a suspension which was obtained by suspending Raney nickel (NIKKO RICA CORPORATION, R-200) in methanol after washing 20 ml of the Raney nickel with water. The product was hydrogenated and after filtering the reaction mixture, the filtrate was distilled under reduced pressure to remove the solvent. The residue was resolved in methylenechloride. The solution thus formed was washed with water, dried over anhydrous magnesium sulfate, and concentrated under reduce pressure to provide 10 g of a yellow oily material. The product was subjected to column chromatography (silica gel: 150 g; chloroform:methanol=20:1) to provide 7.4 g of colorless oily material of 3-aminooctadecanoic acid t-butyl ester (Compound A). The Compound A was dissolved in 30 ml of methylenechloride and after cooling the solution to −10° C. and adding 2.87 ml of TEA, a solution of 5.63 g of hyxadecanoyl chloride in 20 ml of methylenechloride was added dropwise thereto. After stirring the mixture for 1 hour, the reaction mixture was poured into ice-water to separate the product. The separated methylene chloride solution was washed with a saline solution, cooled dil. hydrochloric acid, a saline solution, 5% sodium hydrogencarbonate solution, and a saline solution succesively, dried over anhydrous magnesium sulfate. The drying agent was removed by filtration, and the filtrate was concentrated under reduced pressure to provide 10.9 g of a white solid material of 3-hexadecanamidooctadecanoic acid t-butyl ester [Compound B].

[Compound A]

NMR(CDCl$_3$, δ) 0.87((3H, t, J=6 Hz), 1.1~1.4(28H, m), 1.46(9H, s), 2.18(2H, m), 3.1(1H, m).

[Compound B]

IR(KBr) 3280, 2910, 2830, 1720, 1635 cm$^{-1}$.

NMR(CDCl$_3$, δ), 0.86(6H, t, J=6 Hz), 1.1~1.7(63H, m), 2.15(2H, t, J=9 Hz), 2.41(2H, d, J=6 Hz), 4.2(1H, m), 6.05(1H, d, J=10 Hz).

(ii) In 10 ml of methylenechloride was dissolved 10.9 g of Compound B obtained in the above (i) and after cooling to −10° C. and adding dropwise thereto 100 ml of TFA, the mixture was stirred for 1 hour at room temperature. The reaction mixture was concentrated under reduce pressure, and the concentrate was recrystallized from 500 ml of methanol to provide 9.03 g of a white crystal of 3-hexadecaneamidooctadecanoic acid. m.p. 97°–98° C.

IR(KBr) 3270, 2900, 2830, 1720, 1635, 1550 cm$^{-1}$.

NMR(CDCl$_3$, δ) 0.88(6H, t, J=6 Hz), 1.1~1.7(54H, m), 2.18(2H, m), 2.48(2H, d, J=6 Hz), 4.2(1H, m).

EXAMPLE 7

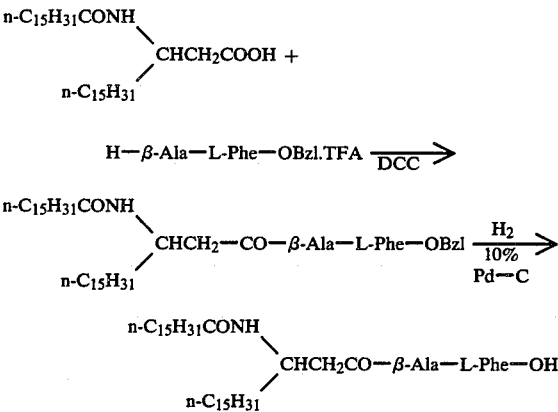

(i) In 30 ml of chloroform was suspended 900 mg of 3-hexadecanamidooctadecanoic acid and 810 mg of β-alanyl-L-phenylalaninebenzyl ester TFA salt and after cooling the suspension to 0° C. and adding thereto 256 μl of TEA and 379 mg of DCC, the mixture was stirred for 30 minutes at 0° C., and then 20 hours at room temperature. To the reaction mixture was added 500 ml of chloroform and after stirring the mixture and removing insoluble matters by filtration, the chloroform solution was washed with a saline solution, cooled dil. hydrochloric acid, and a saline solution, and dried over anhydrous magnesium sulfate. The drying agent was removed by filtration, and the filtrate was distilled under reduced pressure to remove the solvent. 1.85 g of a white solid material was obtained. The material obtained was subjected to column chromatography (silica gel: 150 g; chloroform:methanol=50:1) to provide 1.07 g of a white solid material of N-(3-hexadecanamidooctadecanoyl)-β-alanyl-L-phenylalanine benzyl ester.

IR(KBr) 3280, 2910, 2840, 1735, 1640, 1440 cm$^{-1}$.

NMR(CDCl₃, δ) 1.90(6H, t, J=6 Hz), 1.1~1.8(54H, m), 2.08~2.48(6H, m), 3.06~3.14(4H, m), 4.88(1H, m), 5.2(2H, s), 7.28(5H, s), 7.38(5H, s).

(ii) In 50 ml of methanol and 100 ml of dioxane was suspended 1 g of the compound obtained in the above (i) and the mixture was hydrogenated over 200 mg of 10% Pd-C, under normal pressure at room temperature.

The reaction mixture was filtered and washed with a mixture of chloroform and methanol (1:1). After combining washing solution with the filtrate, the mixture was concentrated under reduced pressure to provide 1 g of grey solid material. The material was dissolved in a mixture of 50 ml of chloroform and 50 ml of methanol, the solution was filtered with Parlite, and the filtrate was concentrated under reduced pressure, and dried to provide a white solid material of N-(3-hexadecanamidooctadecanoyl)-β-alanyl-L-phenylalanine.

mp. 169°-174° C.

IR(KBr) 3275, 2910, 2830, 1715, 1640 cm⁻¹.

NMR(CDCl₃+CD₃OD, δ) 0.88(6H, t, J=6 Hz), 1.1~1.7(54H, m), 2.05~2.44(6H, m), 3.0~3.3(4H, m), 4.0~4.3(1H, m), 4.7(1H, m) 7.25(5H, m).

EXAMPLE 8

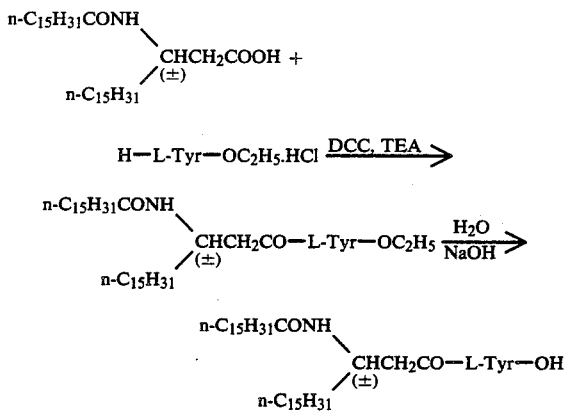

(i) By following the same procedure as in Example 7-(i) using 1 g of 3-hexadecanamidooctadecanoic acid and 467 mg of L-tyrosine ethyl ester hydrochloride, 1.08 g of a white solid material of N-(3-hexadecanamidooctadecanoyl)-L-tyrosine ethyl ester was obtained.

IR(KBr) 3420, 3270, 2900, 2830, 1715, 1640, 1610 cm⁻¹.

NMR(CDCl₃+CD₃OD, δ) 0.88(6H, t, J=6 Hz), 1.1~1.7(57H, m), 2.14(2H, t, J=8 Hz), 2.35(2H, d, J=7 Hz), 2.98(2H, m), 4.05(1H, m), 4.16(2H, q, J=8 Hz), 4.68(1H, t, J=8 Hz), 6.64(2H, d, J=10 Hz), 7.0(2H, dd, J=10 Hz, 2 Hz).

(ii) In 50 ml of ethanol was dissolved in 1.04 g of the compound obtained as above while heating, and after adding thereto 3 ml of 1N sodium hydroxide water solution, the mixture was refluxed for 3 hours. The reaction mixture was concentrated under reduced pressure and after adding to the concentrate 200 ml of water and 600 ml of chloroform, the aqueous layer as acidified to pH 4 with dil. hydrochloric acid and stirred. Precipitates thus formed was collected by filtration to provide 600 mg of a white solid material of N-(3-hexadecanamidooctadecanoyl)-L-tyrosine.

mp. 141°-143° C.

IR(KBr) 3275, 2900, 2830, 1720, 1635 cm⁻¹.

NMR(CDCl₃+CD₃OD, δ) 0.88(6H, t, J=6 Hz), 1.1~1.7(54H, m), 2.14(2H, t, J=8 Hz), 2.35(2H, d, J=7 Hz), 3.03(2H, m), 4.08(1H, m), 4.68(1H, t, J=7 Hz), 6.75(2H, d, J=10 Hz), 7.05(2H, dd, J=10 Hz, 2 Hz).

EXAMPLE 9

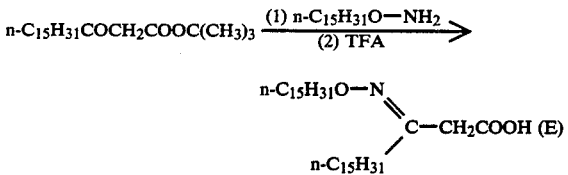

In 150 ml of methanol were dissolved 4.6 g of 3-oxooctadecanoic acid t-butyl ester and 3.3 g of O-pentadecylhydroxylamine and after refluxing the solution, the mixture was distilled to remove methanol. The residue was dissolved in chloroform. The chloroform solution was washed with cooled hydrochloric acid and water, dried over anhydrous magnesium sulfate, and concentrated under reduced pressure to provide 7.41 g of colorless oily material. The material was cooled to 0° C. and after adding dropwise thereto 80 ml of TFA, the mixture was stirred for 1.5 hour at room temperature. The reaction mixture was concentrated under reduced pressure to provide 6.6 g of white solid material. The material was subjected to column chromatography (silica gel: 150 g; first chloroform and then chloroform:melthanol=20:1 v/v) to provide 4.8 g of (E)-3-(pentadecyloxyimino)octadecanoic acid (anti substance).

mp. 65°-67° C.

IR(KBr) 2910, 2830, 1685 cm⁻¹.

NMR(CDCl₃, δ) 0.87(6H, t, J=6 Hz), 1.1~1.7(52H, m), 2.38(2H, t, J=9 Hz), 3.28(2H, s), 4.06(2H, t, 7 Hz).

EXAMPLE 10

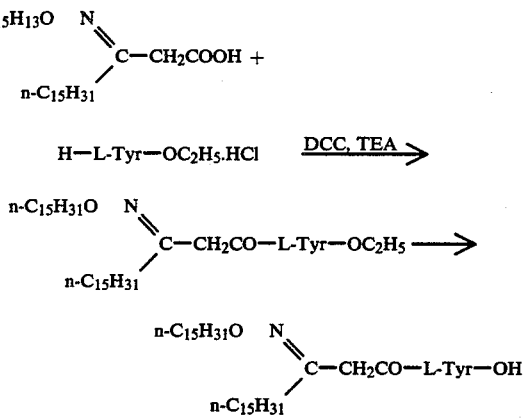

(i) In 15 ml of chloroform were dissolved 1 g of 3-pentadecyloxyiminooctadecanoic acid and 480 mg of L-tyrosine ethyl ester hydrochloride and after the solution to 0° C. and adding 273 μl of TEA and 402 mg of DCC thereto, the mixture was srtirred for 1 hour at 0° C. and then 3 days at room temperature. Precipitates thus formed was removed by filtration and the filtrate was washed with cooled dil. hydrochloric acid, a saline solution, 4% sodium hydrogencarbonate solution and a saline solution successively, dried over anhydrous magnesium sulfate, and concentrated under reduced pressure to provide 1.6 g of a white solid material. The material was recrystallized from a mixture of methanol and ethyl acetate (1:1) to provide 770 mg of N-[3-(pentadecyloxyimino)octadecanoyl]-L-tyrosine ethyl ester.

IR(KBr) 3400, 3275, 2900, 2830, 1720, 1640 cm$^{-1}$.

NMR(CDCl$_3$, δ) 0.84(6H, t, J=6 Hz), 1.1~1.7(55H, m), 2.3(2H, m), 3.05(2H, m), 3.11(2H, s), 4.02(2H, t, J=7 Hz), 4.17(2H, q, J=8 Hz), 4.82(1H, m), 5.68(1H, s), 6.72 (2H, d, J=10 Hz), 6.99(2H, d, J=10 Hz), 6.88(1H, m).

(ii) In 20 ml of methanol was dissolved the compound obtained in the above (i) and after adding thereto 2.2 ml of aqueous 1N-sodium hydroxide solution, the mixture was refluxed for 3 hours. The reaction mixture was concentrated under reduced pressure and after adding to the concentrate 100 ml of chloroform and adjusting the pH to 3 with dil. hydrochloric acid, the chloroform layer separated was washed with water, dried over anhydrous magnesium sulfate, and concentrated under reduced pressure to provide 0.8 g of the residue. The residue was subjected to column chromatography (silicagel: 30 g; chloroform:Methanol=from 20:1 to 2:1) to purify the product. A white waxy material of 470 mg of N-[3-(pentadecyloxyimino)octadecanoyl]-L-tyrosine (a mixture of syn- and anti-substances) was obtained.

IR(KBr) 3290, 2910, 2830, 1690, 1645 cm$^{-1}$.

NMR(CDCl$_3$+CD$_3$OD, δ) 0.88(6H, t, J=6 Hz), 1.1~1.7(52H, m), 2.26 (2H, m), 2.98~3.12(4H, m), 4.02(2H, t, J=7 Hz), 4.7(1H, t, J=7 Hz), 6.75(2H, d, J=10 Hz), 7.02(2H, dd, J=10 Hz, 3 Hz).

EXAMPLE 11

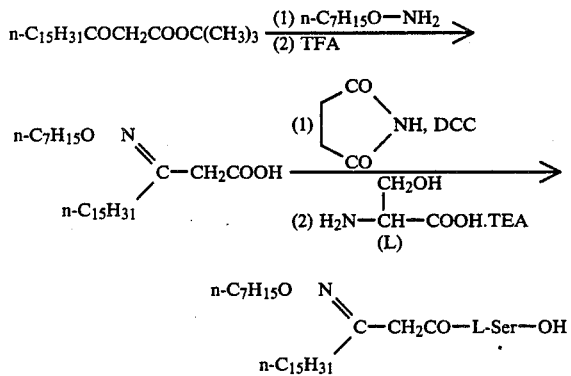

(i) By following the same procedure as in Example 9 using 5 g of 3-oxooctadecanoic acid t-butyl ester and O-heptylhydroxylamine, 3 g of a colorless oil of 3-heptyloxyiminooctadecanoic acid (a mixture of syn- and anti-substances) were obtained.

IR (neat) 2910, 2830, 1705 cm$^{-1}$.

NMR(CDCl$_3$, δ) 0.8~1.0(6H, m), 1.1~1.7(36H, m), 2.28(2H, m), 3.23(0.5H, s), 3.3(1.5H, s), 40.2(2H, m).

(ii) In 20 ml of dioxane was dissolved 3 g of 3-heptyloxyiminooctadecanoic acid and after thereto 0.88 g of HOSU, cooling the mixture to 0° C., and adding 1.57 g of DCC, the mixture was stirred for 1 hour at 0° C. and then for 4 hours at room temperature. Precipitates thus formed was removed by filtration, and the filtrate was concentrated under reduced pressure and the residue formed was dissolved in 50 ml of dimethylformamide. The solution was cooled to 0° C. and after adding thereto 0.84 g of L-serine and 10 ml of an aqueous solution of 1.12 ml of TEA, the mixture was stirred for 24 hours at room temperature. The reaction mixture was concentrated under reduced pressure, and the residue was dissolved in 50 ml of chloroform, washed with a saline solution, cooled dil. hydrochloric acid and then a saline solution, and dried over anhydrous magnesium sulfate, and concentrated under reduced pressure to provide 3 g of a viscous material. The material was subjected to column chromatography (silica gel: 200 g; chloroform:methanol=20:1) to provide 610 mg of a whilte powder of N-[3-(heptyloxyimino)octadecanoyl]-L-serine.

IR(KBr) 3280, 2910, 2830, 1735, 1640 cm$^{-1}$.

NMR(CDCl$_3$, δ) 0.88(6H, t, J=6 Hz), 1.1~1.7(36H, m), 2.40(2H, m), 3.24(2H, s), 4.05(2H, t, J=7 Hz), 4.1(2H, m), 4.60(1H, m), 7.56(1H, m).

EXAMPLE 12

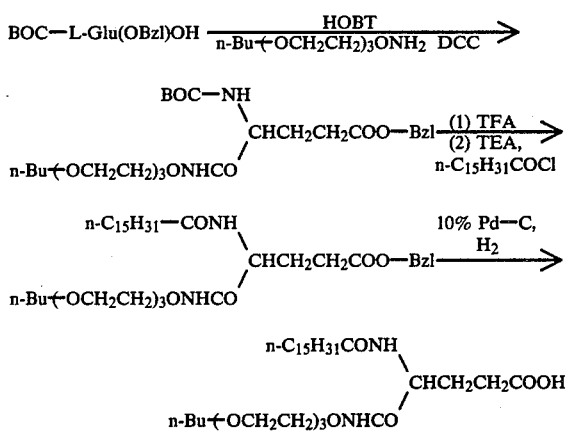

(i) In 20 ml of methylenechloride was dissolved 2 g of N-t-butoxycarbonyl-L-glutamic acid benzyl ester and 877 mg of HOBT and after cooling the solution to 0° C. and adding 1.24 g of DCC, the mixture was stirred for 30 minutes. To the mixture was added 1.33 g of O-(3,6,9-trioxatridecyl)hydroxylamine, and the mixture was stirred for 1 hour under ice-cooling and then 12 hours at room temperature. Precipitates thus formed was removed by filteration and the filtrate was distilled under reduced pressure to remove the solvent. The formed residue was subjected to column chromatography (silica gel: 200 g; chloroform:methanol=100:1) to provide 3.18 g of a colorless oil of (S)-δ-t-butoxycarbonylamino-δ-[N-(3,6,9-trioxatridecyloxy)carbamoyl]-butyric acid benzyl ester.

IR(neat) 3250, 2950, 2920, 2860, 1680~1730(broad) cm$^{-1}$.

NMR(CDCl$_3$, δ) 0.90(3H, t, J=7 Hz) 1.2~1.7(13H, m) 1.9~2.3(2H, m) 1.4~1.6(2H, m) 3.47(2H, t, J=7 Hz) 3.6~3.8(10H, m) 4.08(3H, m) 5.13(2H, s) 5.30(1H, d, J=10 Hz) 7.37(5H, s).

(ii) In 10 ml of methylenechloride was dissolved 1.5 g of the compound obtained in the above (i) and after adding 10 ml of anisole thereto, the mixture was cooled to −10° C. To the mixture was added dropwise 30 ml of TFA, and the mixture was stirred for 1 hour under ice-cooling. The reaction mixture was concentrated under reduced pressure, and benzene was added to the residure. The solution thus formed was concentrated under reduced pressure. The formed residue was dissolved in 20 ml of methylenechloride and after adding 1.18 ml of TEA under ice-cooling and then cooling the mixture to −30° C., a solution of 770 mg of n-hexadecanoylchloride in 10 ml of methylenechloride was added dropwise to the mixture. After stirring the mixture for 20 minutes under ince-cooling, the reaction mixture was poured into ice-water. The mixture was acidified with 1N hydrochloric acid, and extracted with 80 ml of chloroform and 40 ml of chloroform successively. The chloroform layers were combined. The chloroform solution was washed twice with saturated saline solutions and dried over anhydrous magnesium sulfate. The drying agent was removed by filtration, and the filtrate was distilled under reduced pressure to remove the solvent. The formed residue was subjected to column chromatography (silica gel: 100 g; chloroform-methanol=100:1) by v/v ratio) to provide a colorless solid material of 1.5 g of (S)-4-hexadecanamido-4-[N-(3,6,9-trioxatridecyloxy)carbamoyl]butyric acid benzyl ester.

IR(KBr) 3270, 2910, 2840, 1725, 1635 cm$^{-1}$.

NMR(CDCl$_3$, δ) 0.9(6H, m) 1.2~1.7(32H, m) 1.9~2.6(4H, m) 3.47(2H, t, J=7 Hz) 3.6~3.8(10H, m) 4.04(2H, m) 4.40(1H, m) 5.12(2H, s) 6.44(1H, d, J=10 Hz) 7.36(5H, s).

(iii) To a mixture of 30 ml of ethyl acetate and 30 ml of methanol was dissolved 1.41 g of the compound obtained in the above (ii) and the solution was hydrogenated over 140 mg of 10% Pd-C, under normal pressure at room temperature. The reaction mixture was filtered, and the filtrate was concentrated under reduce pressure to provide 1.32 g of colorless material of (S)-4-hexadecanamido-4-[N-(3,6,9-trioxatridecyloxy)carbamoyl]lactic acid.

IR(KBr) 3270, 2910, 2830, 1730, 1700, 1660, 1635 cm$^{-1}$.

NMR(CDCl$_3$, δ) 0.9(6H, m) 1.1~1.7(32H, m) 1.9~2.5(4H, m) 3.47(2H, t, J=7 Hz) 3.6~3.8 (10H, m) 4.08(1H, m) 4.54 (1H, m) 6.71 (1H, d, J=10 Hz).

EXAMPLE 13

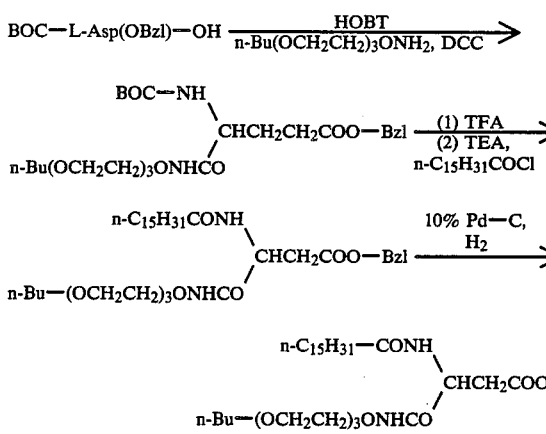

(i) By following the same procedure as in Example 1-(i) using 4 g of N-t-butoxycarbonyl-L-aspartic acid β-benzyl ester and 2.76 g of O-(3,6,9-trioxatridecyl)hydroxylamine, 5.88 g of colorless oil of of (S)-3-t-butoxycarbonylamino-3-[N-(3,6,9-trioxatridecyloxy)carbamoyl]propionic acid benzyl ester was obtained.

IR(neat) 3270, 2950, 2920, 2860, 1660~1730(broad) cm$^{-1}$.

NMR(CDCl$_3$, δ) 0.94(3H, t, J=7 Hz) 1.2~1.7(13H, m) 2.87(2H, dd, J=7 Hz, 4 Hz) 3.48(2H, t, J=7 Hz) 3.6~3.8(10H, m) 4.05(2H, m) 4.50(1H, m) 5.15(2H, s) 5.58(1H, d, J=10 Hz) 7.37(5H, s).

(ii) By following the same procedure as in Example 12-(ii) using 1.5 g of the compound obtained in the above (i), 1.39 g of a colorless solid material of (S)-3-hexadecanamido-4-[N-(3,6,9-trioxatridecyloxy)carbamoyl]propionic acid benzyl ester was obtained.

IR(KBr) 3270, 3220, 2900, 2830, 1720, 1630 cm$^{-1}$.

NMR(CDCl$_3$, δ) 0.9(6H, m) 1.2~1.7(30H, m) 2.2(2H, t, J=8 Hz) 2.84(2H, m) 3.47(2H, t, J=7 Hz) 3.6~3.8 (10H, m) 4.05(2H, m) 4.77(1H, m) 5.15(2H, s) 6.75(1H, d, J=8 Hz) 7.37(5H, s).

(iii) By following the same procedure as in Example 12-(iii) using 1.39 g of the compound obtained in the abve (ii), 1.0 g of colorless solid material of (S)-3-hexadecanamido-4-[N-3,6,9-trioxatridecyloxy)carbamoyl]-propionic acid was obtained.

IR(KBr) 3270, 3200, 2910, 2830, 1700, 1645 cm$^{-1}$.

NMR(CDCl$_3$) 0.9(6H, m) 1.2~1.7(30H, m) 2.24(2H, m) 2.80(2H, m) 3.48(2H, t, J32 7 Hz) 3.6~3.8(10H, m) 4.07(2H, m) 4.80(1H, m) 6.90(1H, d, J=9 Hz).

EXAMPLE 14

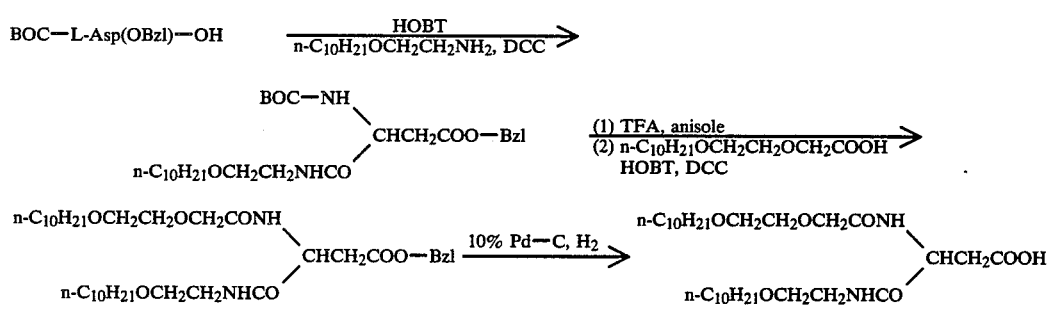

(i) By following the same procedure as in Example 12-(i) using 3.05 g of N-t-butoxycarbonyl-L-aspartic acid β-benzyl ester and 3.05 g of O-decylethanolamine, 5.58 g of colorless oil of (S)-3-t-butoxycarbonylamino-3-(3-oxatridecylcarbamoyl)propionic acid benzyl ester was obtained.

IR(neat) 3280, 2930, 2840, 1715, 1665 cm$^{-1}$.

NMR(CDCl$_3$, δ) 0.87(3H, t, 6 Hz), 1.2~1.7(25H, m) 2.7(1H, dd, J=7 Hz, 19 Hz) 3.10(1H, dd, J=5 Hz, 19 Hz) 3.3~3.5(6H, m) 4.5(1H, m) 5.12(2H, s) 5.62(1H, m) 6.75 (1H, ) 7.35(5H, s).

(ii) In 5 ml of methylenechloride was dissolved 800 mg of the compound obtained in the above (i) and after adding 5 ml of anisole and adding dropwise 10 ml of TFA under ice-cooling, the mixture was stirred for 1 hour under ice-cooling. The reaction mixture was concentrated under reduce pressure. To the formed residue was added 50 ml of ether and 50 ml of water, and the pH of the mixture was adjusted to 9-10 with 4% an aqueous soidum hydrogencarboante solution. The aqueous layer separated was extracted with 30 ml of ether and after combining the ether layers separated, the ether solution was washed with a saturated saline solution, dried over anhydrous magnesium sulfate, and concentrated under reduced pressure to provide a colorless solid material.

On the other hand, 411 mg of 3,6-dioxahexadecanoic acid and 216 mg of HOBT were dissolved in 10 ml of methylenechloride and after adding thereto 330 mg of DCC under ice-cooling, the mixture was stirred for 30 minutes under ice-cooling. To the reaction mixture was added a solution of the above clorless solid material obtained as above in 10 ml of methylenechloride, and the mixture was stirred for 24 hours at room temperature. The reaction mixture was filtered and the filtrate was washed successively with 0.1N hydrochloric acid, a saturated saline slution, aqueous 4% sodium hydrogencarboante solution and a saturated saline solution, dried over anhydrous magnesium sulfate, and concentrated under reduced pressure to provide a colorless solid material. The material was subjected to column choromatography (silica gel: 30 g; chloroform:methanol=100:1 by v/v ratio) to provide a colrless solid material of 840 mg of (S)-3-(3,6-dioxahexadecanamido)-3-(3-oxatridecylcarbamoyl)propionic acid benzyl ester.

IR(KBr) 3290, 2920, 2840, 1730, 1645 cm$^{-1}$.

NMR(CDCl$_3$, δ) 0.88(6H, m) 1.2~1.7(32H, m) 2.9(2H, m) 3.32~3.70(12H, m) 4.03 (2H, s) 4.90(1H, m) 5.15(2H, s) 6.75(1H, m) 7.35(5H, s) 7.72(1H, d, J=10 Hz).

(iii) By following the same procedure as in Example 12-(iii) using 830 mg of the compound obtained in the above (ii), 620 mg of a colorless solid material of (S)-3-(3,6-dioxahexadecanamido)-3-(3-oxatridecylcarbamoyl)propionic acid was obtained.

m.p. 70°~71° C.

IR(KBr) 3320, 3275, 2910, 2840, 1710, 1675 cm$^{-1}$.

NMR(CDCl$_3$, δ) 0.88(6H, m) 1.2~1.7(32H, m) 2.87(2H, m) 3.35~3.70(12H, m) 4.06(2H, s) 4.88(1H, m) 6.94(1H, m) 7.76(1H, d, J=10 Hz).

EXAMPLE 15 ing thereto 13 ml of anisole and adding dropwise thereto 40 ml of TFA under ice-cooling, the mixture was stirred for 2 hours under ice-cooling. The reaction mixture was concentrated under reduced pressure to provide a residue. In 10 ml of methylenechloride were dissolved 957 mg of 3.6,9-trioxahexadecanoic acid and 540 mg of HOBT, and after adding thereto 803 mg of DCC under ice-cooling, the mixture was stirred for 30 mintes. To the mixture were added a solution of the above residue and 560 μl of TEA, in 10 ml of methylenechloride and the mixture was stired for 24 hours at room temperature. The reaction mixture was filtered, and the filtrate was washed with 0.5N-hydrochloric acid, a saturated saline solution, 4% aqueous sodium hydrogencarbonate solution, and a saturated saline solution, succesively; and after drying over anhydrous magnesium sulfate, the solution was concentrated under reduced pressure to provide an oily material. The material was subjected to column chromatography (silica gel: 100 g; ethyl acetate-hexane=1:2 by v/v ratio) to provie 1.06 g of a colorless solid material of (S)-3-tetradecylcarbamoyl-3-(3,6,9-trioxahexadecanamido)propinic acid benzyl ester.

IR(KBr) 3300, 2920, 2840, 1730, 1660 cm$^{-1}$.

NMR(CDCl$_3$, δ) 0.88(6H, m) 1.2~1.7(32H, m) 2.90(2H, m) 3.21(2H, m) 3.46(2H, t, J=7 Hz) 3.6~3.78(8H, m) 4.04(2H, s) 4.87(1H, m) 5.16(2H, s) 6.54(1H, m).

(ii) By following the same procedure as in Example 12-(iii) using 1 g of the compound obtained in the above i), 750 mg of a white solid material of (S)-3-tetradecylcarbamoyl-3-(3,6,9-trioxahexadecanamido)propionic acid was obtained.

IR(KBr) 3290, 2910, 2830, 1715, 1650, 1630 cm$^{-1}$.

NMR(CDCl$_3$, δ) 0.88(6H. m) 1.2~1.7(32H, m) 2.76 (1H, dd, J=7 Hz, 18 Hz) 3.03 (1H, dd, J=6 Hz, 18 Hz) 3.24(2H, m) 3.53(2H, t, J=7 Hz) 3.6~3.8(8H, m) 4.06(2H, d, J=3 Hz) 4.82(1H, m) 6.60(1H, m) 7.87(1H, d, J=10 Hz).

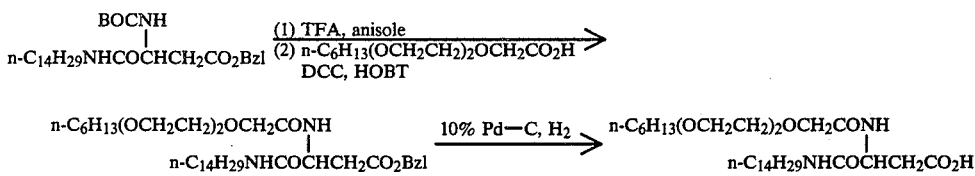

(i) In 13 ml of methylenechloride was dissolved 2 g of the compund obtained by Example 1-(i) and after add-

EXAMPLE 16

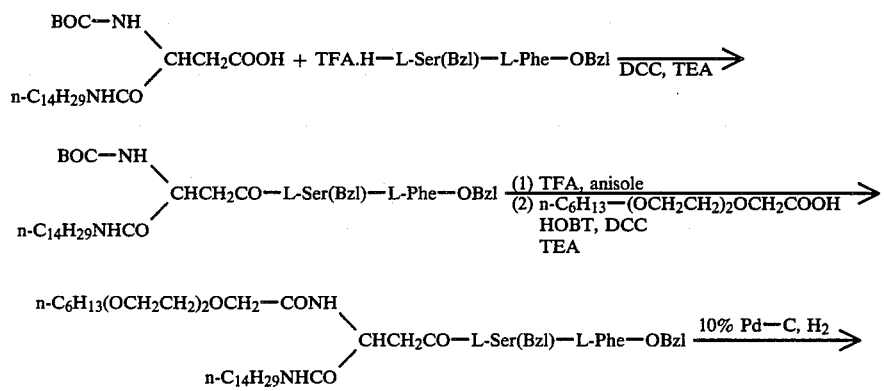

-continued

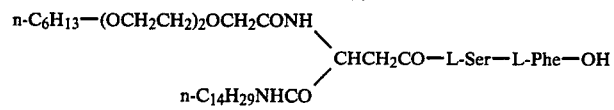

(i) In 20 ml of methylenechloride were dissolved 1.73 mg of the compound obtained by Example 1-(ii) and 2.21 g of L-seryl-L-phenylalanine benzyl ester TFA salt and after adding thereto 0.57 ml of TEA and 845 mg of DCC under ice-cooling, the mixture was stirred for 24 hours at room temperature. To the reaction mixture was added chloroform upto 300 ml, and precipitates were removed by filtration. The filtrate was washed with cooled 0.5N hydrochloric acid, a saturated saline solution, 4% aqueous soidum hydrogencarboante soltuion, and a saturated saline solution, succesively, dried with anhydrous sodium sulfate, and concentrated under reduced pressure. The formed residue was subjected to column chromatography (silica gel: 100 g; chloroform-methanol=100:1 v/v ratio) to provide 1.97 g of a white solid material of N-[(S)-3-t-butoxycarboamido-3-tetradecylcarbamoylpropionyl]-L-O-benzylseryl-L-phenylalanine benzyl ester.

IR(KBr) 3280, 2910, 2840, 1720, 1685, 1635 cm$^{-1}$.

NMR(CDCl$_3$, δ) 0.88(3H, t, J=6 Hz) 1.08~1.70(33H, m) 2.50(1H, dd, J=7 Hz, 17 Hz) 2.85(1H, dd, J=5 Hz, 17 Hz) 3.0~3.3(4H, m) 3.48(1H, dd, J=10 Hz, 8 Hz) 3.86(1H, dd, J=10 Hz, 5 Hz) 4.3~4.6(2H, m) 4.45(2H, s) 4.85(1H, m) 5.12(2H, s) 6.0(1H, m) 6.56(1H, m) 6.76(1H, m) 6.9~7.44(15H, m).

(ii) By following the same procedure as in Example 15-(i) using 980 mg of the compound obtained in the above (i) and 293 mg of 3,6,9-hexadecanoic acid, 900 mg of a white solid material of N-[(S)-3-tetradecylcarbamoyl-3-(3,6,9-trioxadecanamido)propionyl]-L-O-benzylseryl-L-phenylalanine benzyl eater.

IR(KBr) 3270, 2920, 2840, 1715, 1635 cm$^{-1}$.

NMR(CDCl$_3$, δ) 0.88(6H, m) 1.16~1.70(32H, ,) 2.68(2H, m) 3.0~3.24(4H, m) 3.26~3.7(11H, m) 3.87(1H, dd, J=4 Hz, 10 Hz) 4.03(2H, s) 4.44(2H, s) 4.48(1H, m) 4.68~4.96(2H, m) 5.15(2H, s) 7.0~7.4(15H, m).

(iii) In 20 ml of acetic acid was dissolved 900 mg of the compound obtained in the above (ii) and the solution was hydrogenated over 500 mg of 10% Pd-C under normal pressure at room temperature. The reaction mixture was filtered, and the filtrate was concentrated under reduced pressure to provide 560 mg of a white solid material of N-[(S)-3-tetradecylcarbamoyl-3-(3,6,9-trioxahexadecanamido)propionyl]-L-seryl-L-phenylalanine.

m.p. 140°-142° C.

IR(KBr) 3275, 2910, 2840, 1720, 1635 cm$^{-1}$.

NMR(CDCl$_3$, δ) 0.88(6H, m) 1.1~1.7(32H, m) 2.68(2H, m) 3.16(4H, m) 3.37~3.80(12H, m) 3.96(2H, s) 7.22(5H, s).

EXAMPLE 17

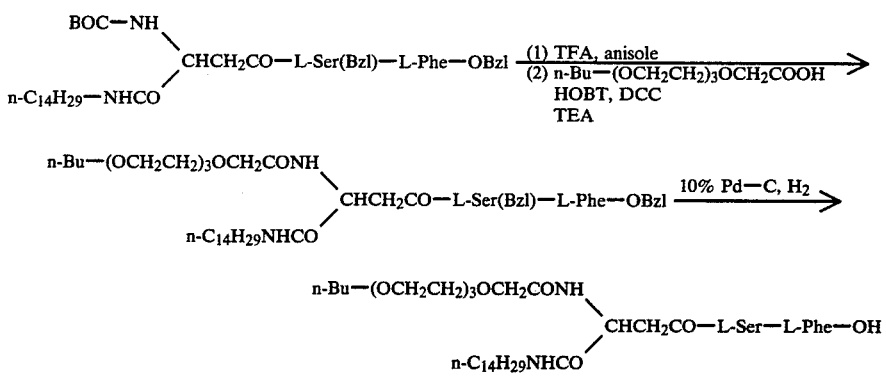

(i) By following the same procedure as in Example 15-(i) using 970 mg of the compound obtained in Example 16-(i) and 304 mg of 3,6,9,12-tetraoxahexadecanoic acid, 1.08 g of a white solid material of N-[(S)-3-tetradecylcarbamoyl-3-(3,6,9,12-tetraoxahexadecanamido)propionyl]-L-O-benzylseryl-L-phenylalanine benzyl ester was obtained.

IR(KBr) 3270, 3060, 2910, 2840, 1715, 1635 cm$^{-}$.

NMR(CDCl$_3$, δ) 0.8~1.0(6H, m) 1.15~1.65(28H, m) 2.7(2H, m) 3.0~3.2(4H, m) 3.44(2H, t, J=7 Hz) 3.4~3.7(13H, m) 3.88(1H, dd, J=4 Hz, 10 Hz) 4.03(2H, s) 4.44(2H, s) 4.5(1H, m) 4.72~5.00(2H, s) 7.0~7.6(15H, m).

(ii) By following the same procedure as in Example 16-(iii) using 760 mg of the compound obtained in the above (i), 500 mg of a white solid material of N-[(S)-3-tetradecylcarbamoyl-3-(3,6,9,12-tetraoxahexadecanamido)propinyl]-L-seryl-L-phenylalanine was obtained.

IR(KBr) 3270, 3060, 2910, 2840, 1720, 1630 cm$^{-1}$.

NMR(CDCl$_3$, δ) 0.8~1.0(6H, m) 1.0~1.7(28H, m) 2.7(2H, m) 3.16(4H, m) 3.3~3.9(16H, m) 3.98(2H, s) 4.4~5.0(3H, m) 7.21(5H, s).

EXAMPLE 18

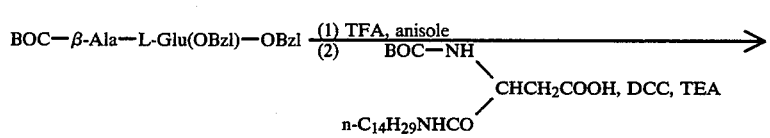

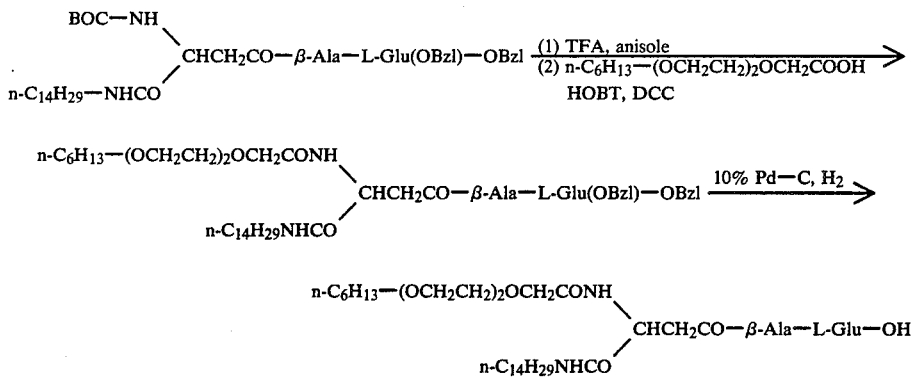

(i) In 16 ml of methylenechloride was dissolved 1.63 g of N-t-butoxycarbonyl-β-alanyl-L-glutamic acid α,γ-dibenzylester and after adding thereto 16 ml of anisole, cooling the mixture of −30° C. and adding dropwise thereto 32 ml of TFA, the mixture was stirred for 2 hours under ice-cooling. The mixture was concentrated under reduced pressure, and 50 ml of ether and 50 ml of hexane were added to the residue to treat it. The upper solvent of the residue was removed by decantation, and insoluble matters of β-alanyl-L-glutamic acid dibenzyl ester TFA salt was obtained. In 20 ml of methylenechloride were dissolved the above diester and 1.4 g of the compound obtained by Example 1-(ii) and after adding thereto 458 μl of TEA and 680 mg of DCC under cooling, the mixture was stirred for 3 days at room temperature. The reaction mixture was filtered, and the filtrate was washed with cooled 0.5N hydrochloric acid, a saturated saline solution, 4% aqueous sodium hydrogencarbonate solution, and a saturated soline solution, successively, dried over anhydrous sodium sulfate, and concentrated under reduced pressure to provide a white solid material. The material was subjected to column chromatography (silica gel: 100 g; chloroform:methanol=100:1 by v/v ratio) to provide 1.7 g of a white solid material of N-[3-t-butoxycarboamido-3-tetradecylcarbamoylpropionyl]-β-alanyl-L-glutamic acid dibenzyl ester.

IR(KBr) 3290, 2910, 2840, 1730, 1685, 1640 cm$^{-1}$.

NMR(CDCl$_3$, δ) 0.88(3H, t, J=6 Hz) 1.15~1.60(24H, m) 1.44(9H, s) 2.10~2.76(8H, m) 2.85~3.30(4H, m) 3.9(1H, m) 4.39(1H, m) 4.67(1H, m) 5.10(2H, s) 5.16(2H, s) 6.88(1H, m) 7.31(5H, s) 7.34(5H, s) 7.74(1H, d, J=9 Hz).

(ii) By following the same procedure as in Example 15-(i), using 1.7 g of the compound obtained in the above (i) and 523 mg of 3,6,9-trioxahexadecanoic acid, 1.36 g of a white material of N-[(S)-3-(3,6,9-trioxahexadecanamido)-3-tetradecylcarbamoylpropionyl]-β-alanyl-L-glutamic acid dibenzyl ester was obtained.

IR(KBr) 3280, 3070, 2910, 2840, 1730, 1635 cm$^{-1}$.

NMR(CDCl$_3$, δ) 0.88(6H, m) 1.05~1.70(32H, m) 2.0~2.8(8H, m) 1.9~2.3(4H, m) 3.46(2H, t, J=7 Hz) 3.63(4H, m) 3.75(4H, s) 4.08(2H, s) 4.5~4.84(3H, m) 5.11(2H, s) 5.19(2H, s) 7.02(1H, m) 7.36(5H, s) 7.38(5H, s) 7.75(1H, d, J=10 Hz) 8.90(1H, d, J=9 Hz).

(iii) By following the same procedure as in Example 12-(iii) using 1.3 g of the compound obtained in the above (ii), 1.0 g of a white solid material of N-[(S)-3-tetradecylcarbamoyl-3-(3,6,9-ttioxahexadecanamido)propionyl]-β-alanyl-L-glutamic acid was obtained.

IR(KBr) 3275, 3075, 2910, 2840, 1730, 1635 cm$^{-1}$.

NMR(CDCl$_3$, δ) 0.88(6H, t, J=7 Hz) 1.1~1.7(32H, m) 1.9~2.9(8H, m) 3.2(4H, m) 3.48(2H, t, J=7 Hz) 3.5~3.8(8H, m) 4.06(2H, s) 4.62(1H, m) 4.85(1H, m).

EXAMPLE 19

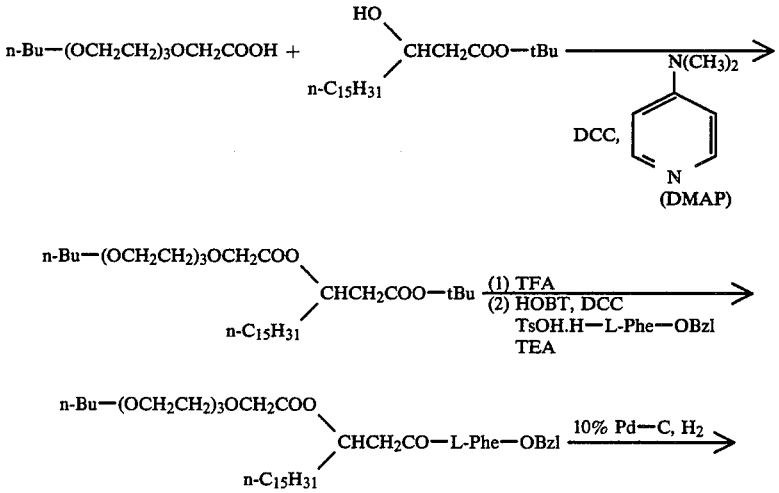

-continued

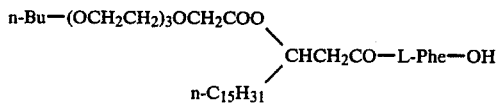

(i) In 200 ml of methylenechloride was dissolved 1.32 g of 3,6,9,12-tetraoxahexadecanoic acid and 1.78 g of 3-hydroxyoctadecanoic acid t-butyl ester and after adding thereto 1.14 g of DCC and 61 mg of DMAP under ice-cooling, the mixture was stirred for 24 hours at room temperature. The reaction mixture was filtered and the filtrate was concentrated under reduced pressure. To the concentrate was added 50 ml of ethyl acetate and the solution formed was washed with cooled 0.5N hydrochloric acid, a saturated saline solution, 4% aqueous sodium hydrogen carbonate solution and a saturated saline solution, succesively, dried over anhydrous sodium sulfate, and concentrated under reduced pressure. The residue thus obtained was subjected to column choromatography (silica gel: 50 g; benzene-ethyl acetate=5:1 by v/v ratio) to provide a colorless liquid of 1.2 g of 3-(3,6,9,12-tetraoxahexadecanoyloxy)oxtadecanoic acid t-butyl ester.

IR(neat) 2910, 2840, 1755, 1730 cm$^{-1}$.

NMR(CDCl$_3$, δ) 0.92(6H, m) 1.2~1.7(32H, m) 1.43(9H, s) 2.49(2H, d, J=7 Hz) 3.47(2H, t, J=7 Hz) 3.58~3.80(12H, m) 4.12(2H, s) 5.30(1H, m).

(ii) To 2.55 g of the compound obtained in the above (ii) was added dropwise 32 ml of TFA while cooling the compound to −30° C. The mixture was stirred for 1 hour at room temperature. The reaction mixture was concentrated under reduced pressure and the residue obtained was dissolved in ether; and the ether solution was washed with water, dried over anhydrous sodium sulfate, and distilled to remove the solvent. 2.24 g of a colorless oily material was obtained. 920 mg of the oily material was dissolved in 10 ml of methylenechloride and after adding thereto 230 mg of HOBT and adding 350 mg of DCC under ice-cooling, the mixture was stirred for 1 hour at room temperature. To the mixture were added 727 mg of L-phenylalanine benzyl ester TsOH salt and 238 µl of TEA under ice-cooling, the mixture was stirred for 20 hours. The reaction mixture was filtered and the filtrate was washed succsesively with cooled 0.5N aquous hydrochloric acid, a saturated saline solution, 4% aquous sodium hydrogencarbonate solution and then a saturated saline solution, dried over anhydrous sodium sulfate, and the solvent was distilled away under reduced pressure to provide a residue. The residue thus obtained was subjected to column chromatography (silica gel: 30 g; chloroform:mthanol=100:1 by v/v ratio) to provide 1.0 g of colorless liquid of N-[3-(3-,6,9,12-tetraoxahexadecanoyloxy)octadecanoyl]-L-phenylalanine benzyl ester.

IR(neat) 3280, 2910, 2840, 1735, 1650 cm$^{-1}$.

NMR(CDCl$_3$, δ) 0.8~1.0(6H, m) 1.1~1.7(32H, m) 1.47(2H, m) 3.10(2H, d, J=7 Hz) 3.46(2H, t, J=7 Hz) 3.60~3.75(12H, m) 4.07(2H, s) 4.90(1H, m) 5.14(2H, s) 5.22(1H, m) 6.22(1H, d, J=8 Hz) 6.96~7.10(2H, m) 7.15~7.45(8H, m).

(iii) In a mixture of 10 ml of methanol and 10 ml of ethyl acetate was dissolved 1 g of the compound obtained in the above (ii) and the solution was hydrogenated over 100 mg of Pd-C under normal pressure at room temperature. The reaction mixture was filtered. The filtrate was concentrated under reduced pressure to provide 770 mg of a white solid material of N-[3-(3,6,9,12-tetraoxahexadecanoyloxy)octadecanoyl]-L-phenylalnine.

IR(KBr) 3320, 2910, 2840, 1735, 1635 cm$^{-1}$.

NMR(CDCl$_3$, δ) 0.8~1.0(6H, m) 1.1~1.7(32H, m) 2.47(2H, m) 3.16(2H, m) 3.48(2H, t, J=7 Hz) 3.55~3.75(12H, m) 4.07(2H, s) 4.85(1H, m) 5.23(1H, m) 6.46(1H, m) 7.24(5H, m).

EXAMPLE 20

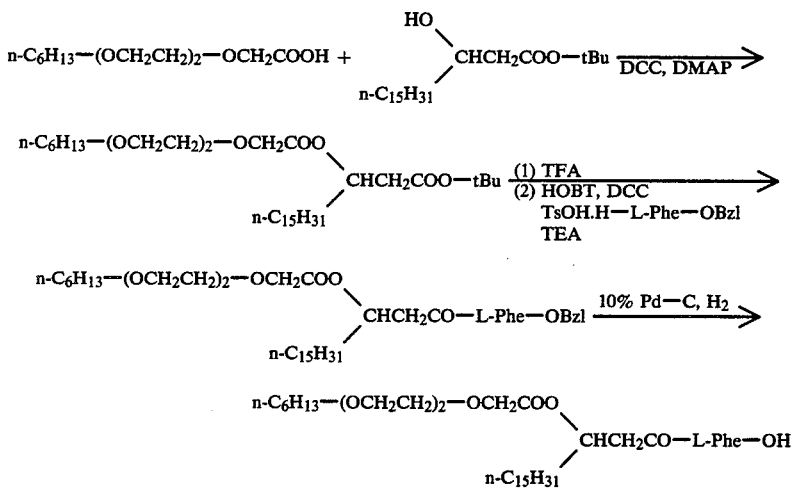

(i) By following the same procedure as in Example 19-(i) using 1.24 g of 3,6,9-trioxapentadecanoic acid and 1.78 g of 3-hydroxyoctadecanoic acid tert-butyl ester, 1.44 g of a colorless liquid of 3-(3,6,9-trioxapentadecanoyloxy)octadecanoic acid tert-butyl ester was obtained.

IR(neat) 2910, 2840, 1750, 1725 cm$^{-1}$.

NMR(CDCl$_3$, δ) 0.88(6H, m) 1.1~1.7(36H, m) 1.42(9H, s) 2.49(2H, d, J=7 Hz) 3.45(2H, t, J=7 Hz) 3.6~3.8(8H, m) 4.08(2H, s) 5.2(1H, m).

(ii) By following the same procedure as in Example 19-(ii) using 1.34 g of the compound obtained in the above (i), 1.23 g of a colorless liquid of N-[3-(3,6,9-trioxapentadecanoyloxy)octadecanoyl]--phenylalanine benzyl ester was obtained.

IR(neat) 3290, 2920, 2840, 1740, 1650 cm$^{-1}$.

NMR(CDCl$_3$, δ) 0.8~1.0(6H, m) 1.2~1.7(36H, m) 2.47(2H, m) 3.10(2H, d, J=7 Hz) 3.45(2H, t, J=7 Hz) 3.55~3.75(8H, m) 4.08(2H, s) 4.92(1H, m) 5.15(2H, m) 5.20(1H, m) 6.19(1H, d, J=9 Hz) 6.95~7.15(2H, m) 7.16~745(8H, m).

(iii) By following the same procedure as in Example 19-(iii) using 1.2 g of the compound obtained in the above (ii), 910 mg of a colorless solid material of N-[3-(3,6,9-trioxapentadecanoyloxy)octadecanoyl]-L-phenylalanine was obtained.

IR(KBr) 3320, 2910, 2840, 1730, 1635 cm$^{-1}$.

NMR(CDCl$_3$, δ) 0.88(6H, m) 1.1~1.7(36H, m) 2.46(2H, m) 3.15(2H, m) 3.46(2H, t, J=7 Hz) 3.55~3.70(8H, m) 4.06(2H, s) 4.83(1H, m) 5.22(1H, m) 6.39(1H, m) 7.1~7.4(5H, m) 7.7(1H, s).

IR(neat) 3300, 2910, 2840, 1730, 1635 cm$^{-1}$.

NMR(CDCl$_3$, δ) 0.88(6H, m), 1.1~1.8(44H, m) 2.46(2H, m) 3.10(2H, d, J=7 Hz), 3.45(2H, t, J=7 Hz), 3.64(4H, m) 4.07(2H, s), 4.9(1H, m) 5.15(2H, s) 5.20(1H, m) 6.12(1H, d, J=9 Hz) 6.95~7.10(2H, m) 7.2~7.4(8H, m).

(iii) By following the same procedure as in Example 19-(iii) using 560 mg of the compound obtained in the above (ii), 390 mg of a white solid material of N-[3-(3,6-dioxahexadecanoyloxy)hexadecanoyl]-L-phenylalanine was obtained.

IR(KBr) 3300, 2910, 2840, 1730, 1640 cm$^{-1}$.

NMR(CDCl$_3$, δ) 0.88(6H, m) 1.2~1.7(44H, m) 2.47(2H, m) 3.14(2H, m) 3.49(2H, t, J=7 Hz) 3.66(4H, s) 4.06(2H, d, J=2 Hz) 4.86(1H, m) 5.20(1H, m) 6.0~6.35(2H, m) 7.26(5H, m).

EXAMPLE 22

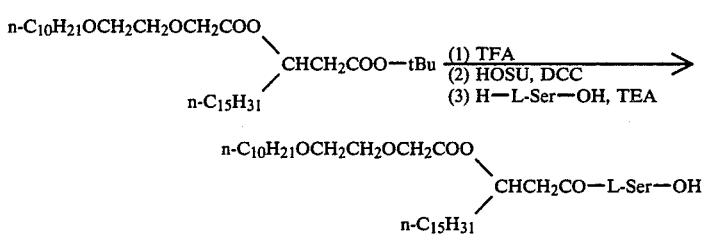

EXAMPLE 21

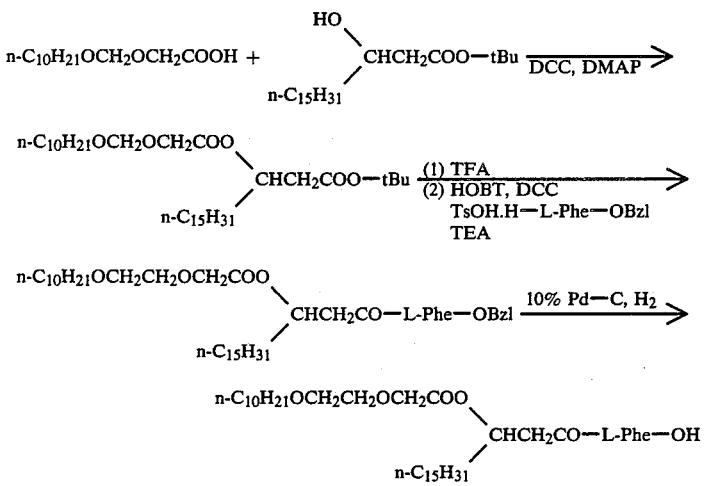

(i) By following the same procedure as in Example 19-(i) using 1.3 g of 3,6-dioxahexadecanoic acid and 1.78 g of 3-hydroxyoctadecanoic acid t-butyl ester, 1.5 g of a color liquid of 3-(3,6-dioxahexadecanoyloxy)octadecanoic acid tert-butyl ester was obtained.

IR(neat) 2910, 2840, 1755, 1730 cm$^{-1}$.

NMR(CDCl$_3$, δ) 0.88(6H, m) 1.1~1.7(44H, m) 1.43(9H, s) 2.50(2H, d, J=7 Hz) 3.47(2H, t, J=7 Hz) 3.67(4H, m) 4.13(2H, s) 5.11(1H, m).

(ii) By following the same procedure as in Example 19-(ii) using 800 mg of the compound obtained in the above (i), a colorless liquid of 560 mg of N-[3-(3,6-dioxahexadecanoyloxy)octadecanoyl]-L-phenylalanine benzyl ester was obtained.

20 ml of TFA was added dropwise to 750 mg of the compound obtained by Example 21-(i) under ice-cooling, and the resultant mixture was stirred for 2 hours at room temperature. The mixture was concentrated under reduced pressure. The formed residue was dissolved in 50 ml of ether, washed with water, and dried over anhydrous magnesium sulfate. The solvent was distilled away under reduced pressure to provide a colorless liquid. After adding thereto 138 mg of HOSU and in 15 ml of dioxane, and adding thereto 249 mg of DCC under ice-cooling, the mixture was stirred for 4 hours at room temperature. The reaction mixture was filtered and the filtrate was concentrated under reduced pressure. The residue thus obtained was dissolved in 20 ml of DMF.

The solution was cooled to 0° C. and a solution of 127 mg of L-serine and 170 μl of TEA in 20 ml of water was added to the solution. The mixture was stirred for 2 days at room temperature. The reaction mixture was concentrated under reduced pressure, and 30 ml of water was added to the formed residue. The formed solution was acidified with 0.1N hydrochloric acid, and extracted twice each time with 50 ml of chloroform. The chlorform layers were combined, washed twice with a saline solution, and dried over anhydrous sodium sulfate, and then concentrated under reduced pressure to provdie a pasty residue. The residue obtained was subjected to column chromatography (silica gel: 50 g; chloroform:methanol=100:1 by v/v ratio) to provide 200 mg of a white solid material of N-[3-(3,6-dioxahexadecanoyloxy)octadecanoyl]-L-serine.

IR(KBr) 3300, 2910, 2840, 1735, 1640 cm$^{-1}$.

NMR(CDCl$_3$, δ) 0.8~1.0(6H, m) 1.1~1.8(44H, m) 2.58(2H, m) 3.50(2H, t, J=7 Hz) 3.68(4H, m) 4.0(2H, m) 4.18(2H, s) 4.65(1H, m) 5.42(2H, m) 7.05(1H, m).

EXAMPLE 23 troleum ether, the residue was subjected to column chromatography and eluted with methanol-chloroform (5:95 by v/v ratio) to provide 500 mg of 3-(6-decanamidohexanoyloxy)octadecanoic acid.

IR (KBr) 3300, 2900, 2830, 1720, 1695, 1620 cm$^{-1}$.

NMR (CDCl$_3$, δ) 0.90 (6H, t, J=6 Hz), 1.00~1.80 (48H, m) 2.08~2.40 (4H, m), 2.56 (2H, d, J=8 Hz), 3.08~3.40 (2H, m), 5.10~5.46 (1H, m).

(iii) 485 mg of the compound obtained as above was mixed with 10 ml of methylenechloride. 375 mg of β-alanyl-L-phenylalanine benzyl ester TFA salt and 0.11 ml of TEA and 175 mg of DCC were added successively to the mixture under ice-cooling. After 30 minutes, ice-bath was removed and the mixture was stirred overnight. Precipitates formed were removed by filtration, the filtrate was washed with water, dried over anhydrous magnesium sulfate. The solvent was distilled off under reduced pressure and the residue thus formed

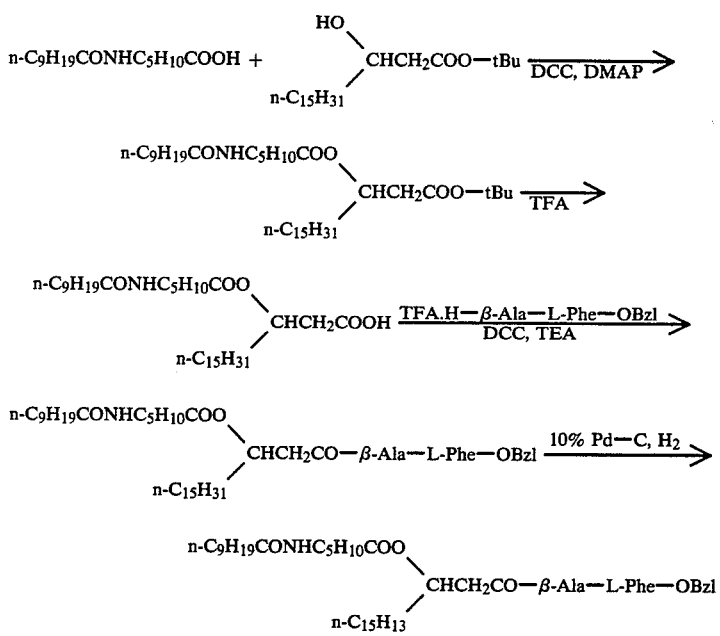

(i) 1.57 g of 3-hydroxyoctadecanoic acid t-butyl ester and 1.30 g of 6-decanamidohexanoic acid were mixed with 30 ml of methylenechloride and after adding thereto 50 mg of DMAP and 930 mg of DCC while stirring, the mixture was stirred for 2 days at room temperature. Precipitates formed were removed by filtration and the filtrate was washed with 10 ml of 0.1N hydrochloric acid, and then washed twice with water, dried over anhydrous magnesium sulfate, and concentrated. The concentrate was subjected to column chromatography and eluted with chloroform to provide 610 mg of 3-(6-decanamidohexanoyloxy)octadecanoic acid t-butyl ester.

(ii) To 700 mg of the compound obtained in the above (i) was added 8 ml of TFA, and the mixture was stirred for 2 hours at room temperature. TFA was distilled off under reduced pressure and after decantation with pewas subjected to silicangel column chromatography and eluted with methanol:chloroform (5:95 by v/v ratio) to provide 730 mg of N-[3-decanamidohexanoyloxy)octadecanoyl]-β-alanyl-L-phenylalanine benzyl ester.

(iv) In a mixture of 30 ml of tetrahydrofuran and 10 ml of methanol was dissolved 705 mg of the compound obtained in the above (iii). The compound was hydrogenated over 80 mg of 10% Pd-C, and the catalyst was removed by filteration. The solvent was distilled off to provide 660 mg of N-[3-decanamidohexanoyloxy)octadecanoyl]-β-alanyl-L-phenylalanine.

IR (KBr) 3290, 2910, 2840, 1720, 1635 cm$^{-1}$.

NMR (CDCl$_3$, δ) 0.88 (6H, t, J=6 Hz), 1.04~2.00 (48H, m), 200~2.52 (8H, m) 3.04~3.48 (6H, m), 4.64~4.92 (1H, m), 5.04~5.28 (1H, m), 7.24 (5H, s).

EXAMPLE 24

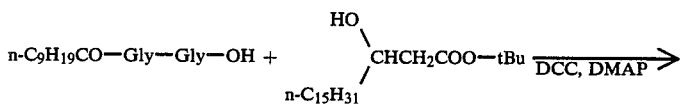

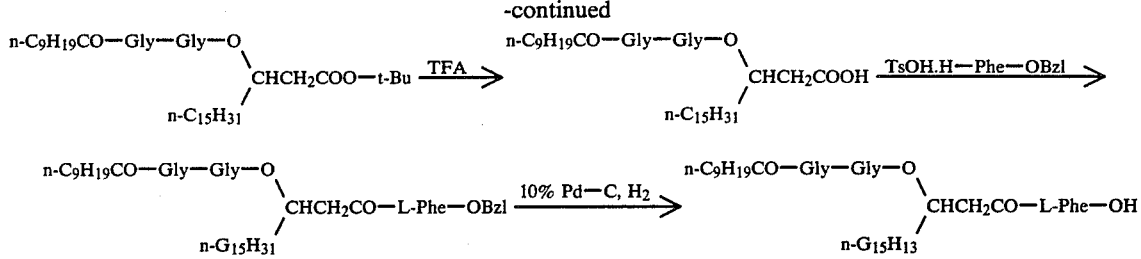

(i) 1.96 g of 3-hydroxyoctadecanoic acid tert-butyl ester and 1.43 g of N-octanoylglycylglycine were mixed with 40 ml of methylenechloride. By following the same procedure as in Example 23-(i) after adding 60 mg of DMAP and 1.14 g of DCC, 970 mg of 3-(N-octanoylglycylglycyloxy)octadecanoic acid tert-butyl ester was obtained.

IR (KBr) 3280, 2920, 2840, 1730, 1660, 1630 cm$^{-1}$.
NMR (CDCl$_3$, δ) 0.88 (6H, t, J=6 Hz), 1.04~2.00 (51H, m), 2.10~2.40 (2H, m), 2.50 (2H, d, J=8 Hz), 3.88~4.28 (4H, m), 5.12~5.40 (1H, m).

(ii) By treating 770 mg of the ester compound obtained as above in the same procedure as in Example 23-(ii) with 8 ml of TFA, a carboxylic acid (free compound) was formed. After drying the product, 2 ml of methylenechloride was added thereto, and 530 mg of L-phenylalanine benzyl ester p-toluenesulfonic acid salt was mixed with the product. To the mixture were added 0.17 ml of TEA and 255 mg of DCC under ice-cooling while stirring. The formed mixture was stirred overnight at room temperature. Precipitates thus formed was removed by filtration, and the filtrate was washed with water, dried and subjected to silica gel column chromatography and eluted with methanol-chloroform (5:95 by v/v ratio) to provide 316 mg of N-[3-(N-decanoylglycylglycyloxy)octadecanoyl]-L-phenylalanine benzyl ester.

300 mg of the formed ester compound as above was dissolved in a mixture of 20 ml of tetrahydrofuran and 10 ml of methanol. By following the same procedure as in Example 23-(iv), 270 mg of N-[3-(N-decanoylglycylglycyloxy)octadecanoyl]-L-phenylalanine was obtained.

IR (KBr) 3300, 2900, 2840, 1740, 1650, 1630 cm$^{-1}$.
NMR (CDCl$_3$, δ) 0.88 (6H, t, J=6 Hz), 1.08~1.92 (42H, m), 2.08~2.40 (2H, m), 2.40~2.56 (2H, d, J=8 Hz), 3.04~3.24 (2H, m), 3.80~4.20 (4H, broad), 4.72~5.00 (1H, m), 5.12~5.48 (1H, m), 7.28 (5H, s).

EXAMPLE 25

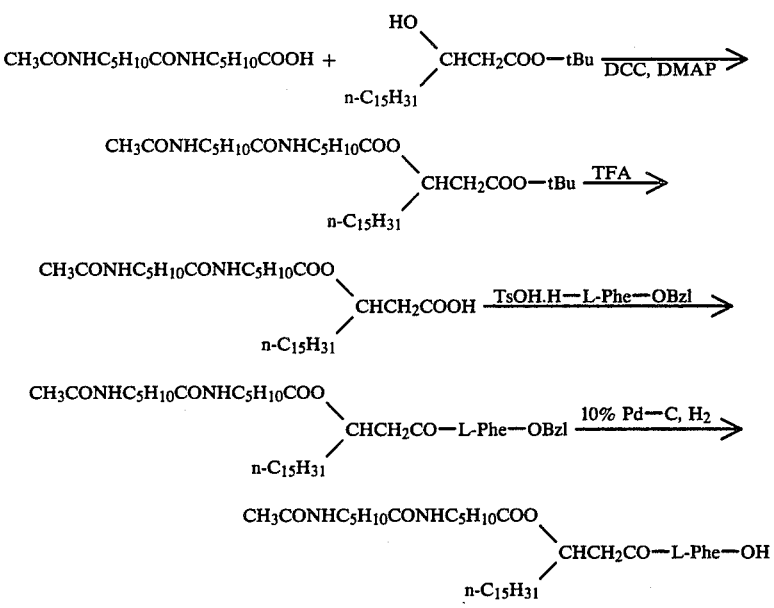

(i) 2.35 g of 3-hydroxyoctadecanoic acid t-butyl ester and 1.80 g of 6-(6-acetamidohexanamido)hexanoic acid were mingled in 40 ml of methylenechloride and after adding thereto 80 mg of DMAP and 1.36 g of DCC, the mixture was treated in the same manner as in Example 23-(i) to provide 1.82 g of 3-[6-(6-acetamidohexanamido)hexanoyloxy]octadecanoic acit t-butyl ester.

IR (KBr) 3280, 3070, 2920, 2850, 1730, 1660 cm$^{-1}$.
NMR (CDCl$_3$, δ) 0.92 (3H, t, J=6 Hz), 1.08~1.80 (49H, m), 1.96 (3H, s), 2.04~2.52 (6H, m), 3.00~3.36 (4H, m), 5.04~5.28 (1H, m).

(ii) 1.80 g of the above ester compound was treated with 8 ml of TFA to convert the ester to free carboxylic acid and after adding thereto 5 ml of methylenechloride, 1.20 g of L-phenylalanine benzyl ester TsOH salt, 0.4 ml of TEA and 590 mg of DCC, the mixture was trated in the same manner as in Example 14-(ii) to provide 740 mg of N-[3-[6-(6-acetamidohexanamido)hexanoyloxy]octadecanoyl]-L-phenylalanine benzyl ester. 660 mg of the ester compound thus were dissolved in a mixture of 30 ml of tetrahydrofuran and 15 ml of methanol and after carrying out catalytic reduction by using 100 mg of 10% Pd-C and treating in the same manner as in Example 23-(iv), 450 mg of N-[3-[6-(6-acetamidohex-anamido)hexanoyloxy]octadecanoyl]-L-phenylalanine was obtained.

IR (KBr) 3280, 3070, 2920, 2850, 1730, 1650, 1630 cm$^{-1}$.

NMR (CDCl$_3$, δ) 0.96 (3H, t, J=6 Hz), 1.08~1.92 (40H, m), 2.00 (3H, s), 2.08~2.48 (6H, m), 3.04~3.48 (6H, m), 4.76~4.92 (1H, m), 5.08~5.20 (1H, m), 7.24 (5H, s).

EXAMPLE 26

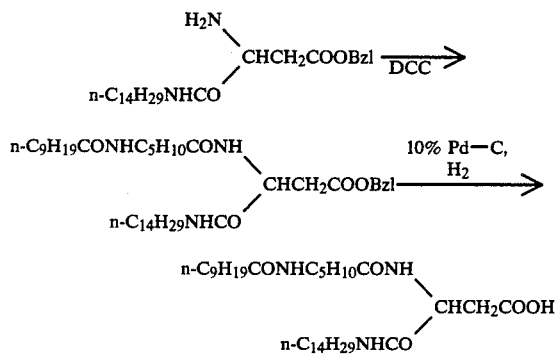

820 mg of (S)-3-amino-3-tetradecylcarbamoylpropionic acid benzyl ester and 520 mg of 6-decanamidohexanoic acid were mingled in 10 ml of methylenechloride and after adding thereto 400 mg of DCC while stirring under ice-cooling and removing ice-bath 30 minutes thereafter, the mixture was stirred overnight.

Precipitates thus formed were removed by filtration, the filtrate was washed with water, dried over anhydrous magnesium sulfate, concentrated, and subjected to silica gel column chromatography. The product was eluted with ethyl acetate-chloroform (1:9—1:1 by v/v ratio) to provide 600 mg of (S)-3-(6-decanamidohexanamido)-3-tetradecylcarbamoylpropionic acid benzyl ester. 1.00 g of the ester compound obtained was dissolved in a mixture of 30 ml of tetrahydrofuran and 10 ml of methanol and after carrying out catalytic reduction by using 100 mg of 10% Pd-C and removing the catalyst by filtration, the solvent was distilled off to provide 670 mg of (S)-3-(6-decanamidohexanamido)-3-tetradecylcarbamoylpropionic acid.

IR (KBr) 3300, 2900, 2840, 1720, 1690, 1630 cm$^{-1}$.

NMR (CDCl$_3$+CD$_3$OD, δ) 0.88 (6H, t, J=6 Hz), 1.04~1.88 (44H, m), 2.04~2.40 (4H, m), 2.72 (2H, d, J=8 Hz), 3.04~3.36 (4H, m), 4.60~4.84 (1H, m).

EXAMPLE 27

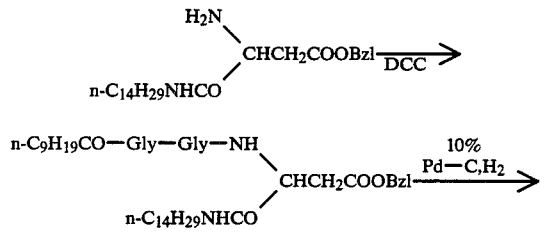

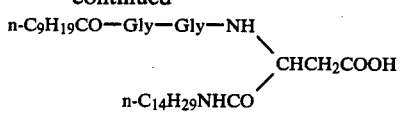

780 mg of (S)-3-amino-3-tetradecylcarbamoylpropionic acid benzyl ester and 490 mg of N-decanoylglycylglycine were mingled in 10 ml of DMF and after adding thereto 380 mg of DCC, the mixture was treated in the same manner as in Example 26. The product was eluted with ethyl acetate-chloroform-methanol (5:5:1 by v/v ratio) to provide 170 mg of (S)-3-(N-decanoylglycylglycylamido)-3-tetradecylcarbamoylpropionic acid benzyl ester.

380 mg of the ester compound thus obtained was dissolved in a mixture of 20 ml of tetrahydrofuran and 10 ml of methanol and after treating the mixture in the same manner as in Example 26, 320 mg of (S)-3-(N-decanolylglycylglycylamido)-3-tetradecylcarbamoylpropionic acid was obtained.

IR (KBr) 3280, 3050, 2900, 2830, 1705, 1650 cm$^{-1}$.

NMR (CDCl$_3$+CD$_3$OD, δ) 0.88 (6H, t, J=6 Hz), 1.08~2.00 (38H, m), 2.08~2.44 (2H, m), 2.84 (2H, d, J=8 Hz), 3.04~3.36 (2H, m), 3.84~4.12 (4H, broad), 4.64~4.88 (1H, m).

EXAMPLE 28

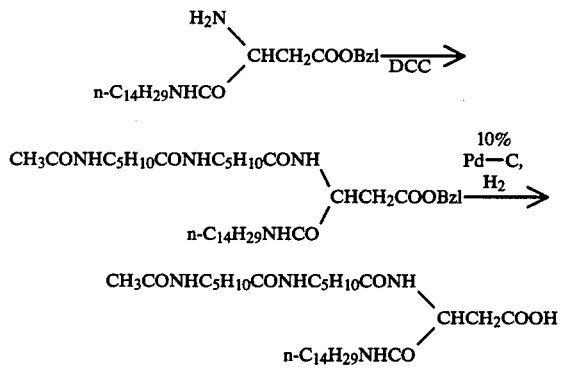

2.1 g of (S)-3-amino-3-tetradecylcarbamoylpropionic acid benzyl ester and 1.5 g of 6-(6-acetamidohexanamido)hexanoic acid were mingled in 10 ml of methylene chloride and after adding thereto 1.1 g of DCC and treating the mixture in the same manner as in Example 26, the product was subjected to silica gel column chromatography, and was eluted with methanol-chloroform (1:3 by v/v ratio) to provide 250 mg of (s)-3-[6-(6-acetamidohexanamido)hexanamido]-3-tetradecylcarbamoylpropionic acid benzyl ester.

250 mg of the ester compound thus obtained was dissolve in a mixture of 10 ml of tetrahydrofuran and 15 ml of methanol and after treating the mixture in the manner as in Example 26, 210 mg of (S)-3-[6-(6-acetamidohexanamido)hexanamido]-3-tetradecylcarbamoylpropionic acid.

(KBr) 3270, 3070, 2910, 2840, 1720, 1630 cm$^{-1}$.

NMR (CDCl$_3$+CD$_3$OD, δ) 0.88 (3H, t, J=6 Hz), 1.04~1.96 (36H, m) 2.00 (3H, s), 2.08~2.48 (4H, m), 2.50~2.86 (2H, m), 3.08~3.40 (6H, m) 4.52~4.80 (1H, m).

EXAMPLE 29

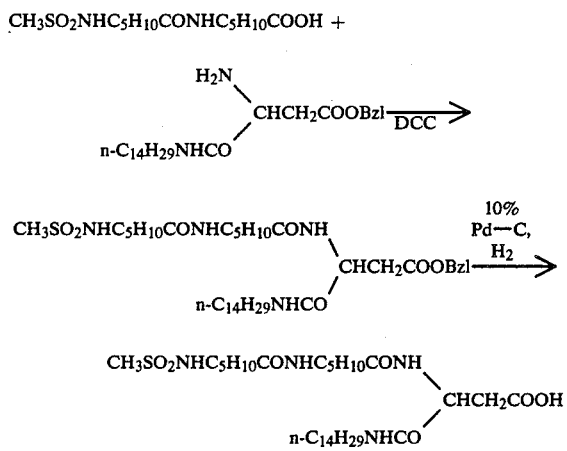

1.05 g of (S)-3-amino-3-tetradecylcarbamoylpropionic acid benzyl ester and 1.00 g of 6-(6-methanesulfonamidohexanamido)hexanoic acid were mingled in 20 ml of methylenechloride and after adding thereto 500 mg of DCC and treating the mixuture in the same manner as in Example 26, 140 mg of (S)-3-[6-(6-methanesulfonamidohexanamido)hexanamido]-3-tetradecylcarbamoylpropionic acid benzyl ester was obtained.

35 mg of the ester compound thus obtained was dissolved in 10 ml of methanol and after treating the mixture in the same manner as in Example 26, 110 mg of (S)-3-[6-(6-methanesulfonamidohexanamido)hexanamido]-3-tetradecylcarbamoylpropionic acid was obtained.

IR (KBr) 3280, 2920, 2850, 1730, 1640 cm$^{-1}$.

NMR (CDCl$_3$+CD$_3$OD, δ) 0.92 (3H, t, J=6 Hz), 1.08~2.00 (36H, m) 2.04~2.50 (4H, m) 2.50~2.80 (2H, m), 2.96 (3H, s), 3.04~3.40 (6H, m), 4.60~4.80 (1H, m).

What is claimed is:

1. A fatty acid derivative selected from the group consisting of:
    N-[3-(3,6-Dioxahexanoyloxy)octadecanoyl]-L-phenylalanine,
    N-[3-(3,6-Dioxahexanoyloxy)octadecanoyl]-L-serine,
    N-[3-(3,6,9-Trioxapentadecanoyloxy)octadecanoyl]-L-phenylalanine,
    N-[3-(3,6,9,12-Tetraoxahexadecanoyloxy)octadecanoyl]-L-phenylalanine, and
    (S)-3-(3,6-Dioxahexadecanamide)-3-(3-oxatridecylcarbamoyl)propionic acid.

2. N-[3-(3,6-Dioxahexanoyloxy)octadecanoyl]-L-phenylalanine.

3. N-[3-(3,6-Dioxahexanoyloxy)octadecanoyl]-L-serine.

4. N-[3-(3,6,9-Trioxapentadecanoyloxy)octadecanoyl]-L-phenylalanine.

5. N-[3-(3,6,9,12-Tetraoxahexadecanoyloxy)octadecanoyl]-L-phenylalanine.

6. (S)-3-(3,6-Dioxahexadecanamide)-3-(3-oxatridecylcarbamoyl)propionic acid.

7. A pharmaceutical composition useful for the treatment of thrombotic diseases which contains a pharmaceutically acceptable carrier and a pharmaceutically effective amount for the treatment of such diseases of the fatty acid derivative of claim 1.

8. A method for the treatment of thrombotic diseases which comprises administering to a patient afflicted with such diseases a fibrinolytically effective amount of the composition of claim 7.

9. The method of claim 8 wherein said composition is administered in a dose of from 5–5,000 mg/kg per day.

10. The method of claim 8 wherein said composition is administered in a dose of from 10–1,000 mg/kg per day.

* * * * *